United States Patent
Conn et al.

(10) Patent No.: US 10,710,997 B2
(45) Date of Patent: ***Jul. 14, 2020

(54) ISOQUINOLINE AMIDE AND ISOQUINOLINE AMIDE-SUBSTITUTED COMPOUNDS AS MGLUR4 ALLOSTERIC POTENTIATORS, COMPOSITIONS, AND METHODS OF TREATING NEUROLOGICAL DYSFUNCTION

(71) Applicant: Vanderbilt University, Nashville, TN (US)

(72) Inventors: P. Jeffrey Conn, Brentwood, TN (US); Craig W. Lindsley, Brentwood, TN (US); Corey R. Hopkins, Bennington, NE (US); Andrew Felts, Brentwood, TN (US); Aaron M. Bender, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/694,501

(22) Filed: Sep. 1, 2017

(65) Prior Publication Data

US 2018/0057491 A1 Mar. 1, 2018

Related U.S. Application Data

(60) Provisional application No. 62/382,665, filed on Sep. 1, 2016.

(51) Int. Cl.
| | |
|---|---|
| *C07D 471/04* | (2006.01) |
| *A61K 31/5377* | (2006.01) |
| *A61K 45/06* | (2006.01) |
| *A61K 31/496* | (2006.01) |
| *A61K 31/541* | (2006.01) |
| *A61K 31/4545* | (2006.01) |
| *A61K 31/4725* | (2006.01) |
| *A61K 31/553* | (2006.01) |
| *A61K 31/47* | (2006.01) |

(52) U.S. Cl.
CPC ........ *C07D 471/04* (2013.01); *A61K 31/4545* (2013.01); *A61K 31/47* (2013.01); *A61K 31/4725* (2013.01); *A61K 31/496* (2013.01); *A61K 31/5377* (2013.01); *A61K 31/541* (2013.01); *A61K 31/553* (2013.01); *A61K 45/06* (2013.01)

(58) Field of Classification Search
CPC .................................................... C07D 471/04
See application file for complete search history.

(56) References Cited

U.S. PATENT DOCUMENTS

| | | |
|---|---|---|
| 8,658,650 B2 | 2/2014 | Conn et al. |
| 8,759,377 B2 | 6/2014 | Conn et al. |
| 8,779,157 B2 | 7/2014 | Conn et al. |
| 8,912,336 B2 | 12/2014 | Conn et al. |
| 8,916,584 B2 | 12/2014 | Conn et al. |
| 9,108,963 B2 | 8/2015 | Conn et al. |
| 9,163,015 B2 | 10/2015 | Conn et al. |
| 9,180,192 B2 | 11/2015 | Conn et al. |
| 9,192,603 B2 | 11/2015 | Conn et al. |
| 9,980,945 B2 | 5/2018 | Conn et al. |
| 2012/0184556 A1 | 7/2012 | Conn et al. |
| 2013/0338154 A1 | 12/2013 | Conn et al. |
| 2018/0022744 A1 | 1/2018 | Conn et al. |
| 2018/0022745 A1 | 1/2018 | Conn et al. |
| 2018/0022746 A1 | 1/2018 | Conn et al. |
| 2018/0057490 A1 | 3/2018 | Conn et al. |
| 2018/0057491 A1 | 3/2018 | Conn et al. |

*Primary Examiner* — Brian E McDowell
(74) *Attorney, Agent, or Firm* — Stites & Harbison PLLC; Richard S. Myers, Jr.

(57) ABSTRACT

Compounds which are useful as allosteric potentiators/positive allosteric modulators of the metabotropic glutamate receptor subtype 4 (mGluR4) of the following formula:

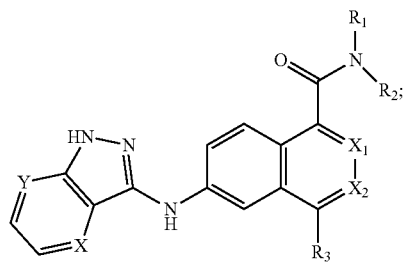

synthetic methods for making the compounds; pharmaceutical compositions comprising the compounds; and methods of using the compounds, for example, in treating neurological and psychiatric disorders or other disease state associated with glutamate dysfunction.

34 Claims, No Drawings

ISOQUINOLINE AMIDE AND ISOQUINOLINE AMIDE-SUBSTITUTED COMPOUNDS AS MGLUR4 ALLOSTERIC POTENTIATORS, COMPOSITIONS, AND METHODS OF TREATING NEUROLOGICAL DYSFUNCTION

This application claims benefit United States Provisional Patent Application Serial No. 62/382,665 which was filed on Sep. 1, 2016, the entire disclosures of which are incorporated herein by this reference.

BACKGROUND

The amino acid L-glutamate (referred to herein simply as glutamate) is the principal excitatory neurotransmitter in the mammalian central nervous system (CNS). Within the CNS, glutamate plays a key role in synaptic plasticity (e.g., long term potentiation (the basis of learning and memory)), motor control and sensory perception. It is now well understood that a variety of neurological and psychiatric disorders, including, but not limited to, schizophrenia general psychosis and cognitive deficits, are associated with dysfunctions in the glutamatergic system. Thus, modulation of the glutamatergic system is an important therapeutic goal. Glutamate acts through two distinct receptors: ionotropic and metabotropic glutamate receptors. The first class, the ionotropic glutamate receptors, is comprised of multi-subunit ligand-gated ion channels that mediate excitatory post-synaptic currents. Three subtypes of ionotropic glutamate receptors have been identified, and despite glutamate serving as agonist for all three receptor subtypes, selective ligands have been discovered that activate each subtype. The ionotropic glutamate receptors are named after their respective selective ligands: kainate receptors, AMPA receptors and NMDA receptors.

The second class of glutamate receptor, termed metabotropic glutamate receptors, (mGluRs), are G-protein coupled receptors (GPCRs) that modulate neurotransmitter release or the strength of synaptic transmission, based on their location (pre- or post-synaptic). The mGluRs are family C GPCR, characterized by a large (~560 amino acid) "venus fly trap" agonist binding domain in the amino-terminal domain of the receptor. This unique agonist binding domain distinguishes family C GPCRs from family A and B GPCRs wherein the agonist binding domains are located within the 7-strand transmembrane spanning (7TM) region or within the extracellular loops that connect the strands to this region. To date, eight distinct mGluRs have been identified, cloned and sequenced. Based on structural similarity, primary coupling to intracellular signaling pathways and pharmacology, the mGluRs have been assigned to three groups: Group I (mGluR1 and mGluR5), Group II (mGluR2 and mGluR3) and Group III (mGluR4, mGluR6, mGluR7 and mGluR8). Group I mGluRs are coupled through Gαq/11 to increase inositol phosphate and metabolism and resultant increases in intracellular calcium. Group I mGluRs are primarily located post-synaptically and have a modulatory effect on ion channel activity and neuronal excitability. Group II (mGluR2 and mGluR3) and Group III (mGluR4, mGluR6, mGluR7 and mGluR8) mGluRs are primarily located pre-synaptically where they regulate the release of neurotransmitters, such as glutamate. Group II and Group III mGluRs are coupled to Gαi and its associated effectors such as adenylate cyclase.

mGluR4 belongs to the group III mGluR subfamily and is located in predominantly presynaptic locations in the central nervous system (Benitez et al., 2000; Bradley et al., 1996; Bradley et al., 1999; Mateos et al., 1998; Phillips et al., 1997) where it is functions as an auto- and heteroreceptor to regulate the release of both GABA and glutamate. mGluR4 has also been shown to be expressed at a low level in some postsynaptic locations (Benitez et al., 2000). Numerous reports indicate that mGluR4 is expressed in most brain regions, particularly in neurons known to play key roles in functions of the basal ganglia (Bradley et al., 1999; Corti et al., 2002; Kuramoto et al., 2007; Marino et al., 2003a), learning and memory (Bradley et al., 1996), vision (Akazawa et al., 1994; Koulen et al., 1996; Quraishi et al., 2007), cerebellar functions (Makoff et al., 1996), feeding and the regulation of hypothalamic hormones (Flor et al., 1995), sleep and wakefulness (Noriega et al., 2007) as well as many others. There are now a number of literature reports describing a role for mGluR4 modulation in Parkinson's disease (Battaglia et al., 2006; Lopez et al., 2007; Marino et al., 2005; Marino et al., 2003b; Ossowska et al., 2007; Valenti et al., 2003), anxiety (Stachowicz et al., 2006; Stachowicz et al., 2004), motor effects after alcohol consumption (Blednov et al., 2004), neurogenic fate commitment and neuronal survival (Saxe et al., 2007), epilepsy (Chapman et al., 2001; Pitsch et al., 2007; Snead et al., 2000; Wang et al., 2005) and cancer, particularly medulloblastoma (Iacovelli et al., 2004).

In addition, there is evidence that activation of mGluR4 receptors (expressed in islets of Langerhans) would inhibit glucagon secretion (Uehara et al., 2004). Thus, activation of mGluR4 may be an effective treatment for disorders involving defects in glucose metabolism such as hypoglycemia, Type 2 diabetes, and obesity.

Also, there are reports that activation of Group III mGluRs, specifically mGluR4, may be an effective treatment for neuroinflammatory diseases, such as multiple sclerosis and related disorders (Besong et al., 2002).

Also, that activation of Group III mGluRs, specifically mGlu4 positive allosteric modulators (PAMs), may be an effective treatment for neuroinflammatory diseases, such as multiple sclerosis and related disorders (Besong et al., 2002; Taylor et al., 2003; Fallarino et al., 2010).

There are two variants of the mGluR4 receptor which are expressed in taste tissues; and thus activation of mGluR4 may be used as taste enhancers, blockade of certain tastes, or taste agents, flavoring agents or other food additives (Kurihara, 2009; Chaudhari et al, 2009).

Despite advances in mGluR4 research, there is still a scarcity of compounds that effectively potentiate mGluR4 which are also effective in the treatment of neurological and psychiatric disorders associated with glutamatergic neurotransmission dysfunction and diseases, As well as inflammatory central nervous system disorders, medulloblastomas, metabolic disorders and taste enhancing associated with glutamatergic dysfunction and diseases in which mGluR4 receptor is involved. Further, conventional mGluR4 receptor modulators typically lack satisfactory aqueous solubility and exhibit poor oral bioavailability. These needs and other needs are satisfied by the present invention.

SUMMARY

In accordance with the purpose(s) of the invention, as embodied and broadly described herein, the invention, in one aspect, relates to compounds useful as allosteric modulators of mGluR4 receptor activity, methods of making same, pharmaceutical compositions comprising same, and methods of treating neurological and psychiatric disorders associated with glutamate dysfunction, for example Parkinson's disease, using same. Further disclosed are methods and pharmaceutical compositions useful for treating a disease related to mGluR4 activity. In one aspect, the disclosed compounds can affect the sensitivity of mGluR4 receptors to agonists without binding to the orthosteric agonist binding site or acting as orthosteric agonists themselves. A "receptor allosteric agonist", as used herein, is generally defined as a ligand that functions as both an allosteric modulator and as an agonist on its own (though the latter is usually only at higher concentrations). The presence of receptor allosteric agonist (Ago-PAM) activity may offer advantages in various CNS and neurological disorders where the basal glutamatergic tone is low in given brain regions or at a particular synapse.

Disclosed are methods for the treatment of a neurotransmission dysfunction or other disease state associated with mGluR4 activity in a mammal comprising the step of administering to the mammal at least one compound in a dosage and amount effective to treat the dysfunction in the mammal, the compound having a structure represented the following formula:

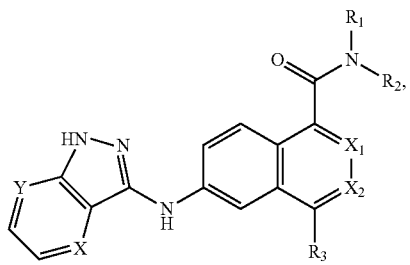

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, cycloheteroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, $CO-R_A$, $SO_2R_A$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_A$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_3$ is H, alkyl, alkene, cycloalkyl, aryl, heteroaryl, alkoxy, hydroxyl, amino, aminoalkoxy, or halogen;
provided that at least one of $X_1$ or $X_2$ is N;
or a pharmaceutically acceptable salt thereof or a pharmaceutically acceptable derivative thereof.

Also disclosed are methods for potentiating mGluR4 activity in a subject comprising the step of administering to the subject at least one compound at least one compound having a structure represented by the following formula:

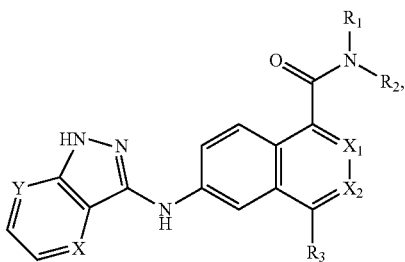

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, cycloheteroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, $CO-R_A$, $SO_2R_A$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_A$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_3$ is H, alkyl, alkene, cycloalkyl, aryl, heteroaryl, alkoxy, hydroxyl, amino, aminoalkoxy, or halogen;
provided that at least one of $X_1$ or $X_2$ is N;
or a pharmaceutically acceptable salt thereof or a pharmaceutically acceptable derivative thereof, in a dosage and amount effective to potentiate mGluR4 receptor activity in the subject.

Also disclosed are methods of potentiating mGluR4 activity in at least one cell comprising the step of contacting at least one cell with at least one compound having a structure represented by the following formula:

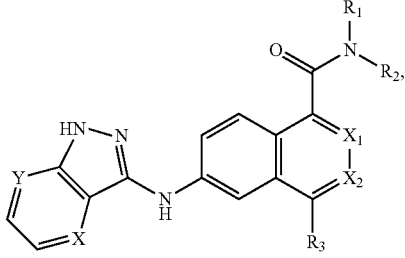

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;

R₂ is optionally substituted with one or more R, and is chosen from cycloaklyl, cycloheteroaryl, aryl, heteroaryl, or together with R₁ forms a 4-7 membered ring optionally substituted with one or more R;

R is independently H, alkyl, alkene, hydroxyl, alkoxy, CF₃, O, O-Me, O-alkyl, O-cycloalkyl, CO—R₄, SO₂R₄, hydroxyl, amino, aminoalkoxy, halogen, SO₂, SO₂-alkyl, SO₂-Me, CONH₂, CN, O, cycloalkyl, cycloheteroalkyl, aryl, heteroaryl;

R₄ is H, alkyl, alkene, hydroxyl, alkoxy, CF₃, O, O-Me, O-alkyl, O-cycloalkyl, hydroxyl, amino, aminoalkoxy, halogen, SO₂, SO₂-alkyl, SO₂-Me, CONH₂, CN, O, cycloalkyl, cycloheteroalkyl, aryl, heteroaryl;

R₃ is H, alkyl, alkene, cycloalkyl, aryl, heteroaryl, alkoxy, hydroxyl, amino, aminoalkoxy, or halogen;

provided that at least one of X₁ or X₂ is N;

or a pharmaceutically acceptable salt thereof or a pharmaceutically acceptable derivative thereof, in an amount effective to potentiate mGluR4 receptor activity in the at least one cell.

Also disclosed are compounds having a structure represented by the following formula:

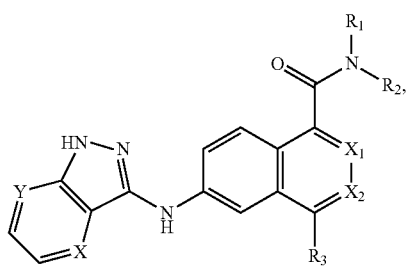

wherein the variables are substituted or unsubstituted and:

X is N, CH, CD, C-alkyl;

X₁ is CH, or N;

X₂ is CH, or N;

Y is N, CH, CD, C-alkyl;

R₁ is H, alkyl, aklene, cycloalkyl, halogen, CF₃, alkoxy, OH, CN, Oalkyl, CH₂F, CHF₂, or together with R₂ forms a 4-7 membered ring optionally substituted with one or more R;

R₂ is optionally substituted with one or more R, and is chosen from cycloaklyl, cycloheteroaryl, aryl, heteroaryl, or together with R₁ forms a 4-7 membered ring optionally substituted with one or more R;

R is independently H, alkyl, alkene, hydroxyl, alkoxy, CF₃, O, O-Me, O-alkyl, O-cycloalkyl, CO—R₄, SO₂R₄, hydroxyl, amino, aminoalkoxy, halogen, SO₂, SO₂-alkyl, SO₂-Me, CONH₂, CN, O, cycloalkyl, cycloheteroalkyl, aryl, heteroaryl;

R₄ is H, alkyl, alkene, hydroxyl, alkoxy, CF₃, O, O-Me, O-alkyl, O-cycloalkyl, hydroxyl, amino, aminoalkoxy, halogen, SO₂, SO₂-alkyl, SO₂-Me, CONH₂, CN, O, cycloalkyl, cycloheteroalkyl, aryl, heteroaryl;

R₃ is H, alkyl, alkene, cycloalkyl, aryl, heteroaryl, alkoxy, hydroxyl, amino, aminoalkoxy, or halogen;

provided that at least one of X₁ or X₂ is N;

or a pharmaceutically acceptable salt thereof or a pharmaceutically acceptable derivative thereof.

Also disclosed pharmaceutical compositions comprising a compound having a structure represented by the following formula:

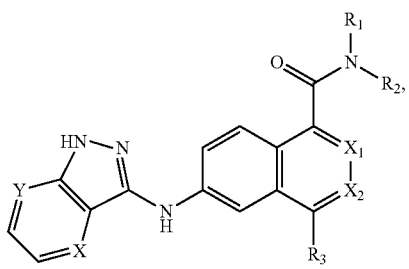

wherein the variables are substituted or unsubstituted and:

X is N, CH, CD, C-alkyl;

X₁ is CH, or N;

X₂ is CH, or N;

Y is N, CH, CD, C-alkyl;

R₁ is H, alkyl, aklene, cycloalkyl, halogen, CF₃, alkoxy, OH, CN, Oalkyl, CH₂F, CHF₂, or together with R₂ forms a 4-7 membered ring optionally substituted with one or more R;

R₂ is optionally substituted with one or more R, and is chosen from cycloaklyl, cycloheteroaryl, aryl, heteroaryl, or together with R₁ forms a 4-7 membered ring optionally substituted with one or more R;

R is independently H, alkyl, alkene, hydroxyl, alkoxy, CF₃, O, O-Me, O-alkyl, O-cycloalkyl, CO—R₄, SO₂R₄, hydroxyl, amino, aminoalkoxy, halogen, SO₂, SO₂-alkyl, SO₂-Me, CONH₂, CN, O, cycloalkyl, cycloheteroalkyl, aryl, heteroaryl;

R₄ is H, alkyl, alkene, hydroxyl, alkoxy, CF₃, O, O-Me, O-alkyl, O-cycloalkyl, hydroxyl, amino, aminoalkoxy, halogen, SO₂, SO₂-alkyl, SO₂-Me, CONH₂, CN, O, cycloalkyl, cycloheteroalkyl, aryl, heteroaryl;

R₃ is H, alkyl, alkene, cycloalkyl, aryl, heteroaryl, alkoxy, hydroxyl, amino, aminoalkoxy, or halogen;

provided that at least one of X₁ or X₂ is N;

or a pharmaceutically acceptable salt thereof or a pharmaceutically acceptable derivative thereof; and a pharmaceutically acceptable carrier.

Also disclosed are methods for potentiating mGluR4 activity in at least one cell comprising the step of contacting at least one cell with at least one disclosed compound in an amount effective to potentiate mGluR4 receptor activity in at least one cell.

Also disclosed are methods for potentiating mGluR4 activity in a subject comprising the step of administering to the subject a therapeutically effective amount of at least one disclosed compound in a dosage and amount effective to potentiate mGluR4 receptor activity in the subject.

Also disclosed are methods for the treatment of a disorder associated with mGluR4 neurotransmission dysfunction or other mGluR4 mediated disease states in a mammal comprising the step of administering to the mammal at least one disclosed compound in a dosage and amount effective to treat the disorder in the mammal.

Also disclosed are methods for making a compound comprising the steps of providing an amine compound having a structure represented by the following formula:

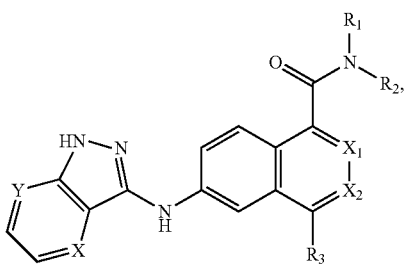

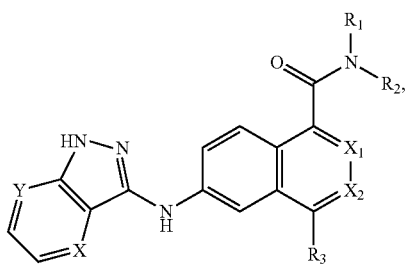

as shown in the Examples below, wherein the variables are defined herein.

Also disclosed are the products of the disclosed methods of making.

Also disclosed are methods for the manufacture of a medicament for potentiating mGluR4 receptor activity in a mammal comprising combining a compound having a structure represented by the following formula:

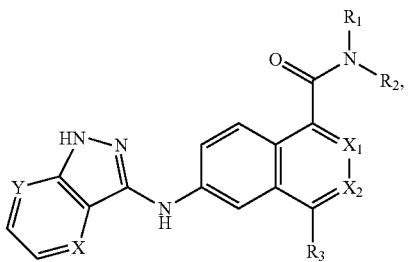

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, cycloheteroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_3$ is H, alkyl, alkene, cycloalkyl, aryl, heteroaryl, alkoxy, hydroxyl, amino, aminoalkoxy, or halogen;
provided that at least one of $X_1$ or $X_2$ is N;
or a pharmaceutically acceptable salt thereof or a pharmaceutically acceptable derivative thereof.

Also disclosed are the products of the disclosed methods for the manufacture of a medicament.

Also disclosed are uses of a compound for potentiating mGluR4 receptor activity in a mammal, wherein the compound has a structure represented by the following formula:

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, cycloheteroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_3$ is H, alkyl, alkene, cycloalkyl, aryl, heteroaryl, alkoxy, hydroxyl, amino, aminoalkoxy, or halogen;
provided that at least one of $X_1$ or $X_2$ is N;
or a pharmaceutically acceptable salt thereof or a pharmaceutically acceptable derivative thereof.

Also disclosed are methods for the treatment of a neurotransmission dysfunction and other disease states associated with mGluR4 activity in a mammal comprising the step of co-administering to the mammal at least one compound in a dosage and amount effective to treat the dysfunction in the mammal, the compound having a structure represented by the following formula:

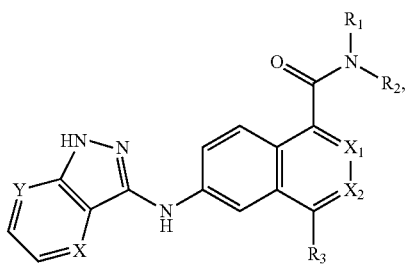

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloaklyl, cycloheteroaryl, aryl, heteroaryl, or together with $R_1$ forms a 4-7 membered ring optionally substituted with one or more R;

R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_3$ is H, alkyl, alkene, cycloalkyl, aryl, heteroaryl, alkoxy, hydroxyl, amino, aminoalkoxy, or halogen;

provided that at least one of $X_1$ or $X_2$ is N;

or a pharmaceutically acceptable salt thereof or a pharmaceutically acceptable derivative thereof with a drug having a known side-effect of increasing metabotropic glutamate receptor activity.

Also disclosed are methods for the treatment of a neurotransmission dysfunction and other disease states associated with mGluR4 activity in a mammal comprising the step of co-administering to the mammal at least one compound in a dosage and amount effective to treat the dysfunction in the mammal, the compound having a structure represented by the following formula:

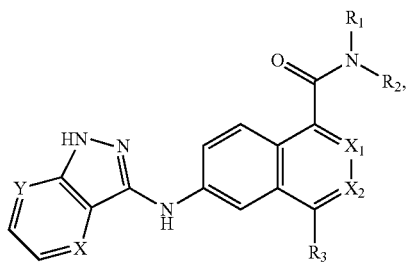

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloaklyl, cycloheteroaryl, aryl, heteroaryl, or together with $R_1$ forms a 4-7 membered ring optionally substituted with one or more R;

R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_3$ is H, alkyl, alkene, cycloalkyl, aryl, heteroaryl, alkoxy, hydroxyl, amino, aminoalkoxy, or halogen;

provided that at least one of $X_1$ or $X_2$ is N;

or a pharmaceutically acceptable salt thereof or a pharmaceutically acceptable derivative thereof with a drug known to treat a disorder associated with increasing metabotropic glutamate receptor activity.

Also disclosed are methods for the treatment of a neurotransmission dysfunction and other disease states associated with mGluR4 activity in a mammal comprising the step of co-administering to the mammal at least one compound in a dosage and amount effective to treat the dysfunction in the mammal, the compound having a structure represented by a Also disclosed are methods for the treatment of a neurotransmission dysfunction and other disease states associated with mGluR4 activity in a mammal comprising the step of co-administering to the mammal at least one compound in a dosage and amount effective to treat the dysfunction in the mammal, the compound having a structure represented by the following formula:

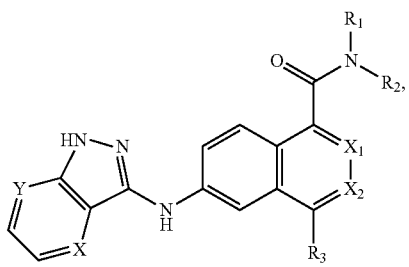

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloaklyl, cycloheteroaryl, aryl, heteroaryl, or together with $R_1$ forms a 4-7 membered ring optionally substituted with one or more R;

R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_3$ is H, alkyl, alkene, cycloalkyl, aryl, heteroaryl, alkoxy, hydroxyl, amino, aminoalkoxy, or halogen;

provided that at least one of $X_1$ or $X_2$ is N;

or a pharmaceutically acceptable salt thereof or a pharmaceutically acceptable derivative thereof with a drug known to treat the neurotransmission dysfunction or other disease states.

Also disclosed are kits comprising a compound having a structure represented by a compound of the present invention.

Also disclosed are methods for the treatment of a neurotransmission dysfunction and other disease states associated with mGluR4 activity in a mammal comprising the step of co-administering to the mammal at least one compound in a dosage and amount effective to treat the dysfunction in the mammal, the compound having a structure represented by the following formula:

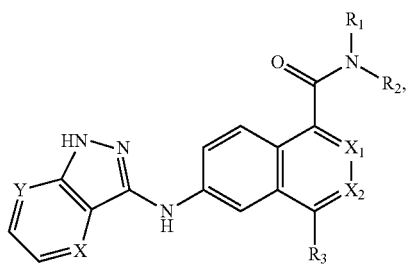

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, cycloheteroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_3$ is H, alkyl, alkene, cycloalkyl, aryl, heteroaryl, alkoxy, hydroxyl, amino, aminoalkoxy, or halogen;
provided that at least one of $X_1$ or $X_2$ is N;
or a pharmaceutically acceptable salt thereof or a pharmaceutically acceptable derivative thereof, and one or more of a drug having a known side-effect of increasing metabotropic glutamate receptor activity, a drug known to treat a disorder associated with increasing metabotropic glutamate receptor activity, and/or a drug known to treat the neurotransmission dysfunction.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "receptor positive allosteric modulator" refers to any exogenously administered compound or agent that directly or indirectly augments the activity of any form (for example, homomeric, heteromeric, oligomeric, or interacting with other proteins or cellular components) of the receptor in the presence or in the absence of the endogenous ligand (such as glutamate, L-serine O-phosphate (L-SOP), other endogenous ligands, other neurotransmitters, etc.) in an animal, in particular a mammal, for example a human. The term "receptor positive allosteric modulator" includes a compound that is a "receptor allosteric potentiator" or a "receptor allosteric agonist," as well as a compound that has mixed activity as both a "receptor allosteric potentiator" and an "mGluR receptor allosteric agonist."

As used herein, the term "receptor allosteric potentiator" refers to any exogenously administered compound or agent that directly or indirectly augments the response of any form (for example, homomeric, heteromeric, oligomeric, or interacting with other proteins or cellular components) of the receptor produced by the endogenous ligand (such as glutamate, L-serine O-phosphate (L-SOP), other endogenous ligands, other neurotransmitters, etc.) when it binds to an allosteric site of any form of receptor in an animal, in particular a mammal, for example a human. The receptor allosteric potentiator binds to a site other than the orthosteric site (an allosteric site) and positively augments the response of the receptor to an agonist. As it is predicted to induce less desensitization of the receptor, activity of a compound as a receptor allosteric potentiator provides advantages over the use of a pure receptor allosteric agonist. Such advantages can include, for example, increased safety margin, higher tolerability, diminished potential for abuse, and reduced toxicity.

As used herein, the term "receptor allosteric agonist" refers to any exogenously administered compound or agent that directly augments the activity of any form (for example, homomeric, heteromeric, oligomeric, or interacting with other proteins or cellular components) of the receptor in the absence of the endogenous ligand (such as glutamate, L-serine O-phosphate (L-SOP), other endogenous ligands, other neurotransmitters, etc.) in an animal, in particular a mammal, for example a human. The receptor allosteric agonist binds to the allosteric glutamate site of the receptor and directly influences the orthosteric site of the receptor. the term "receptor positive allosteric modulator" refers to any exogenously administered compound or agent that directly or indirectly augments the activity of the receptor in the presence or in the absence of the endogenous ligand (such as glutamate, L-serine O-phosphate (L-SOP), other endogenous ligands, other neurotransmitters, etc.) in an animal, in particular a mammal, for example a human. The term "receptor positive allosteric modulator" includes a compound that is a "receptor allosteric potentiator" or a "receptor allosteric agonist," as well as a compound that has mixed activity as both a "receptor allosteric potentiator" and an "mGluR receptor allosteric agonist."

In some aspects of the disclosed methods, the subject has been diagnosed with a need for treatment of one or more neurological and/or psychiatric disorder and/or any other disease state associated with glutamate dysfunction prior to the administering step. In some aspects of the disclosed method, the subject has been diagnosed with a need for potentiation of metabotropic glutamate receptor activity prior to the administering step. In some aspects of the disclosed method, the subject has been diagnosed with a need for partial agonism of metabotropic glutamate receptor activity prior to the administering step. In some aspects, the disclosed methods can further comprise a step of identifying a subject having a need for treatment of a disclosed disorder.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by potentiation of mGluR4 activity" means having been subjected to a physical examination by a person of skill, for example, a physician, and found to have a condition that can be diagnosed or treated by a compound or composition that can favorably potentiate mGluR4 activity. As a further example, "diagnosed with a need for potentiation of mGluR4 activity" refers to having been subjected to a physical examination by a person of skill, for example, a physician, and found to have a condition characterized by abnormal mGluR4 activity. Such a diagnosis can be in reference to a disorder, such as Parkinson's disease, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mGluR4 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the term "receptor allosteric agonist", as used herein, is generally defined as a ligand that functions as both an allosteric modulator and as an agonist on its own (though the latter is usually only at higher concentrations).

As used herein, the term "diagnosed with a need for potentiation of metabotropic glutamate receptor activity" refers to having been subjected to a physical examination by a person of skill, for example, a physician, and found to have a condition that can be diagnosed or treated by potentiation of metabotropic glutamate receptor activity.

As used herein, "diagnosed with a need for partial agonism of metabotropic glutamate receptor activity" means having been subjected to a physical examination by a person of skill, for example, a physician, and found to have a condition that can be diagnosed or treated by partial agonism of metabotropic glutamate receptor activity.

As used herein, "diagnosed with a need for treatment of one or more neurological and/or psychiatric disorder or any disease state associated with glutamate dysfunction" means having been subjected to a physical examination by a person of skill, for example, a physician, and found to have one or more neurological and/or psychiatric disorder associated with glutamate dysfunction.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. SuiTable 3nert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by a formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by a formula —C(O)OH.

The term "ester" as used herein is represented by a formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by a formula -($A^1$O(O)C-$A^2$-C(O)O)$_a$- or -($A^1$O(O)C-$A^2$-OC(O))$_a$, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by a formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by a formula -($A^1$O-$A^2$O)$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by a formula —OH.

The term "ketone" as used herein is represented by a formula $A^1$C(O)$A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by a formula —$N_3$.

The term "nitro" as used herein is represented by a formula —$NO_2$.

The term "nitrile" as used herein is represented by a formula —CN.

The term "silyl" as used herein is represented by a formula —Si$A^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by a formulas —S(O)$A^1$, —S(O)$_2A^1$, —OS(O)$_2A^1$, or —OS(O)$_2$O$A^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by a formula —S(O)$_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by a formula $A^1$S(O)$_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by a formula $A^1$S(O)$A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by a formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

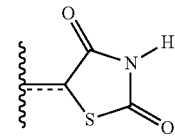

regardless of whether thiazolidinedione is used to prepare the compound. In some aspects the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some aspects, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkyl sulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Typically, inorganic radicals do not comprise metalloids elements such as boron, aluminum, gallium, germanium, arsenic, tin, lead, or tellurium, or the noble gas elements, unless otherwise specifically indicated elsewhere herein.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "hydrolysable residue" is meant to refer to a functional group capable of undergoing hydrolysis, e.g., under basic or acidic conditions. Examples of hydrolysable residues include, without limitation, residues of acid halides or activated carboxylic acids, residues of trialkylsilyl halides, residues of alkyloxymethyl halides, and various other protecting groups known in the art (see, for example, "Protective Groups in Organic Synthesis," T. W. Greene, P. G. M. Wuts, Wiley-Interscience, 1999).

The term "leaving group" refers to an atom (or a group of atoms) with electron withdrawing ability that can be displaced as a stable species, taking with it the bonding electrons. Examples of suitable leaving groups include sulfonate esters, including, but not limited to, triflate, mesylate, tosylate, brosylate, and halides.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. Additionally, unless expressly described as "unsubstituted", all substituents can be substituted or unsubstituted.

In some aspects, a structure of a compound can be represented by a formula:

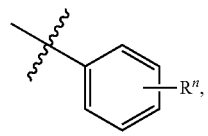

which is understood to be equivalent to a formula:

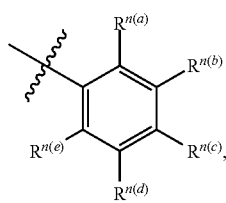

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

The following abbreviations are used herein. DMF: dimethyl formamide. EtOAc: ethyl acetate. THF: tetrahydrofuran. DIPEA or DIEA: diisopropylethylamine. HOBt: 1-hydroxybenzotriazole. EDC: 1-ethyl-3-[3-dimethylaminopropyl]carbodiimide hydrochloride. DMSO: dimethylsulfoxide. DMAP: 4-Dimethylaminopyridine. RT: Room temperature. h: Hours. Min: Minutes. DCM: Dichloromethane. MeCN: Acetonitrile. MeOH: methanol. iPrOH: 2-Propanol. n-BuOH: 1-Butanol.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds, or pharmaceutically acceptable derivatives thereof, useful as potentiators of mGluR4 activity. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using. It is also understood that the disclosed compounds can all be employed as corresponding pharmaceutical compositions.

In one aspect, the invention relates to compounds having a structure represented by the following formula:

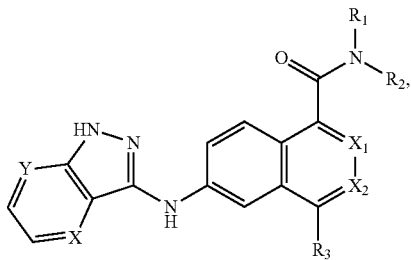

wherein the variables are substituted or unsubstituted and:

X is N, CH, CD, C-alkyl;

$X_1$ is CH, or N;

$X_2$ is CH, or N;

Y is N, CH, CD, C-alkyl;

$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloaklyl, cycloheteroaryl, aryl, heteroaryl, or together with $R_1$ forms a 4-7 membered ring optionally substituted with one or more R;

R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_3$ is H, alkyl, alkene, cycloalkyl, aryl, heteroaryl, alkoxy, hydroxyl, amino, aminoalkoxy, or halogen;

provided that at least one of $X_1$ or $X_2$ is N;

or a pharmaceutically acceptable salt thereof or a pharmaceutically acceptable derivative thereof.

Also disclosed are compounds of the following formula:

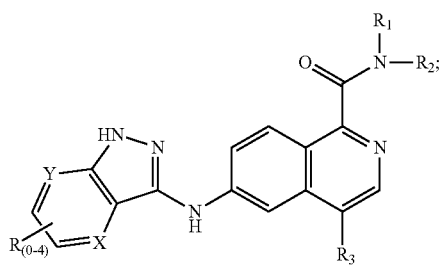

or a pharmaceutically acceptable salt thereof or a pharmaceutically acceptable derivative thereof.

Also disclosed are compounds of the following formula:

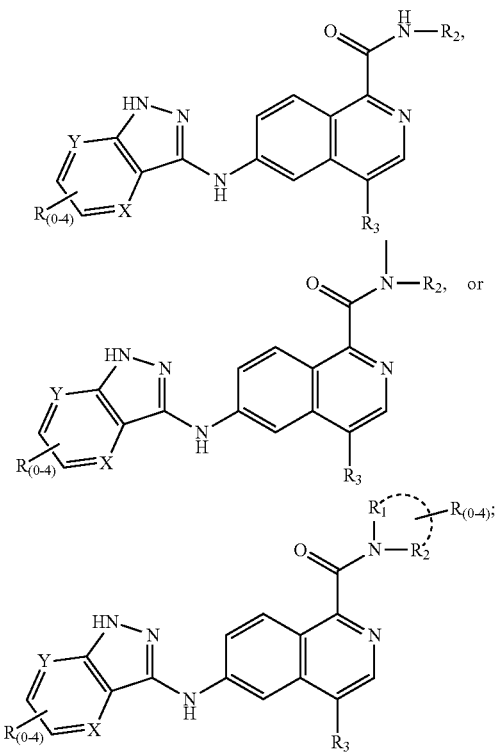

or a pharmaceutically acceptable salt thereof or a pharmaceutically acceptable derivative thereof.

Also disclosed are compounds wherein $R_2$ is optionally substituted with one or more R and is chosen from cyclobutyl, methylsulfonylalkyl, fluorocyclobutyl, difluorocyclobutyl, tetrahydro-furan, or tetrahydro-pyran.

In embodiments of the compounds disclosed herein: cycloalkyl can be cyclobutyl, cyclopropyl, cyclopentyl, cyclohexyl; cycloheteroaryl can be piperazine, pyrrolidin, thiazepin, piperazin-ethanone, azaspiroheptane, oxazepan, tetrahydropyran, morpholino, thiomorpholino, dioxothiomorpholino; and heteroaryl can be pyrazole, triazol, isoxazol, azetidin, thiophen, pyrozolopyrimidine, imidazole, indazole, indazole, pyrazolo-pyridin, and tetramethyl-furopyrazole.

In other embodiments, $R_1$ and $R_2$ together form 4-7 membered cycloalkyl, cycloheteroaryl or bicyclic ([3.3.0], [2.2.0] and [3.1.0]) ring system.

In other embodiments of the compounds disclosed herein, (i) Y is N and X is CH, or (ii) Y is CH and X is N.

Also disclosed are compound of the following formula:

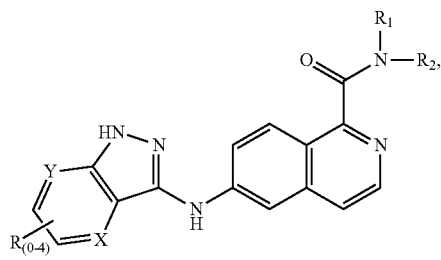

wherein:
$R_1$ is H or alkyl;
$R_2$ is

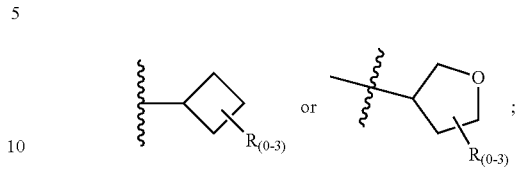

and
(i) Y is N and X is CH, or (ii) Y is CH and X is N; or a pharmaceutically acceptable salt thereof or a pharmaceutically acceptable derivative thereof.

Also disclosed are compounds of the following formula:

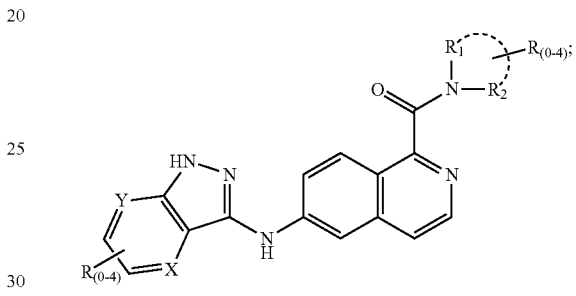

wherein:
$R_1$ and $R_2$ join together to form:

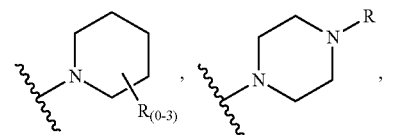

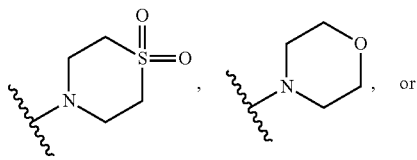

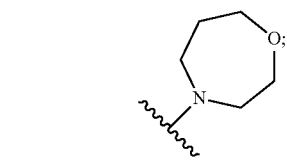

and
(i) Y is N and X is CH, or (ii) Y is CH and X is N; or a pharmaceutically acceptable salt thereof or a pharmaceutically acceptable derivative thereof.

In other embodiments of the compounds disclosed herein, $R_3$ may be trifluoroalkyl, pyrazole, methylpyrazole, pyridine, fluoropyridine, furan, fluoroalkyl, cyclopropyl, cyclopentyl, piperidine, pyrrolidine, morpholine, amino, aminoalkyl-cycloalkyl, fluoro-pyrrolidine, dialkylamino.

In other embodiments, the present invention is directed to a compound of the following formula:
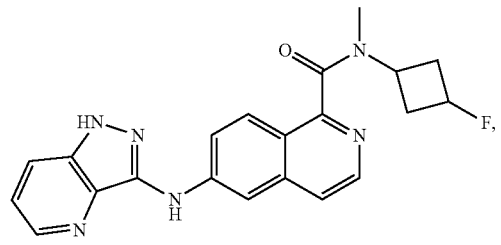
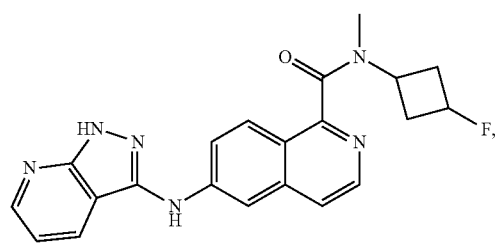
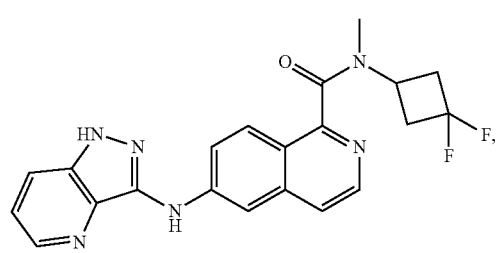
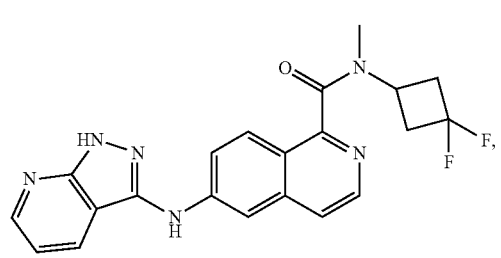
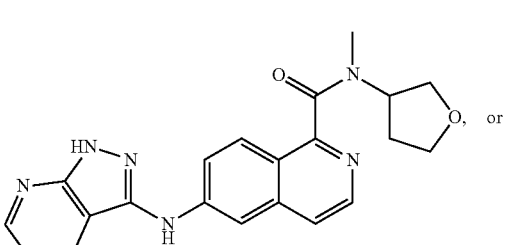, or
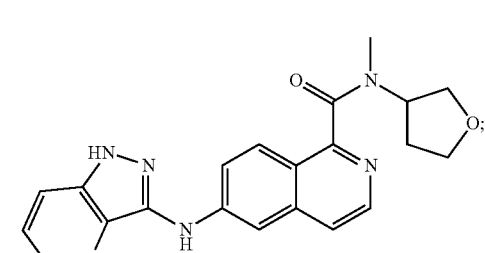;
or a pharmaceutically acceptable salt thereof or a pharmaceutically acceptable derivative thereof.
In other embodiments, the present invention is directed to a compound of the following formula:
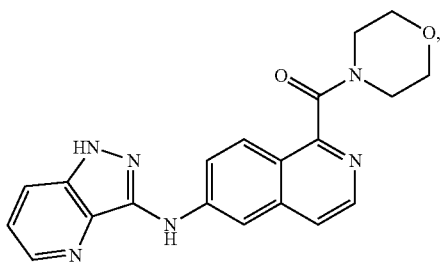
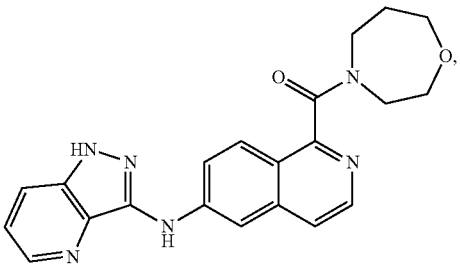
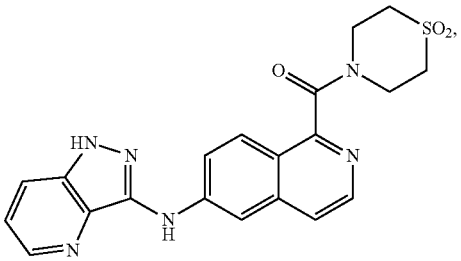
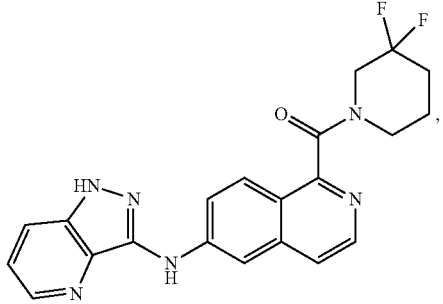
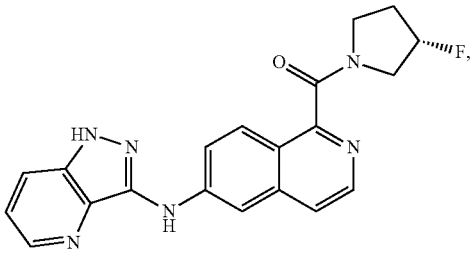
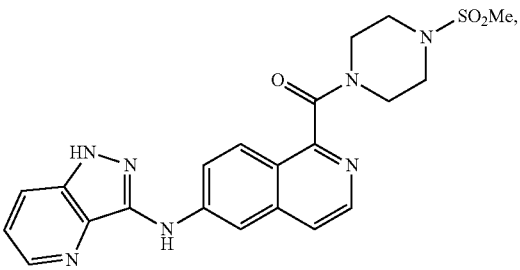

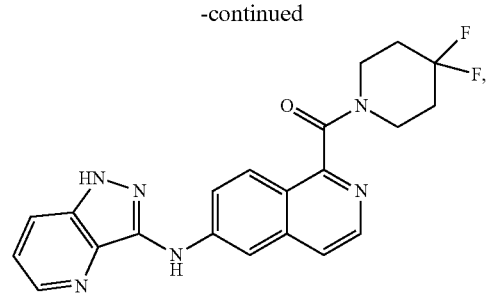
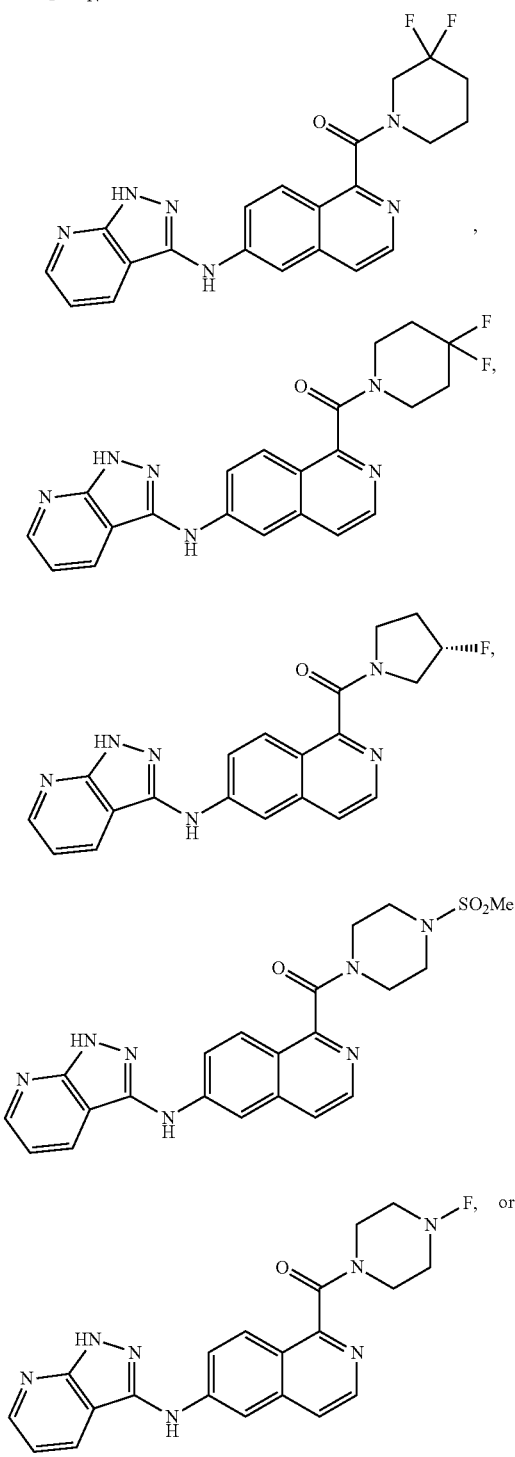
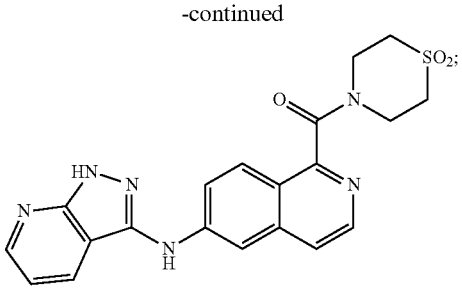
or a pharmaceutically acceptable salt thereof or a pharmaceutically acceptable derivative thereof.
In other embodiments, the present invention is directed to a compound of the following formula:
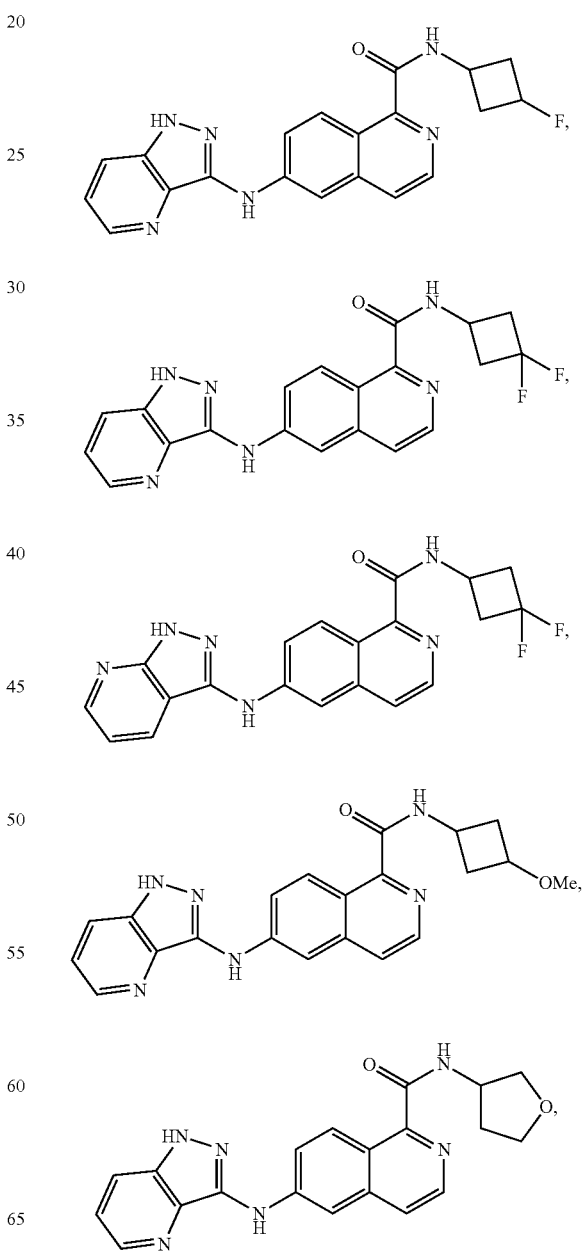

-continued

[chemical structure: N-(3-methoxycyclobutyl) amide of isoquinoline-1-carboxamide with 6-(7H-pyrazolo[3,4-b]pyridin-3-ylamino) substituent]

[chemical structure: N-(tetrahydrofuran-3-yl) amide of isoquinoline-1-carboxamide with 6-(7H-pyrazolo[3,4-b]pyridin-3-ylamino) substituent], or

[chemical structure: N-(3-fluorocyclobutyl) amide of isoquinoline-1-carboxamide with 6-(7H-pyrazolo[3,4-b]pyridin-3-ylamino) substituent];

or a pharmaceutically acceptable salt thereof or a pharmaceutically acceptable derivative thereof.

The compounds disclosed herein can include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The analogs (compounds) of the present disclosure are arranged into several categories to assist the formulator in applying a rational synthetic strategy for the preparation of analogs which are not expressly exampled herein. The arrangement into categories does not imply increased or decreased efficacy for any of the compositions of matter described herein.

C. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

A potentiated amount of an mGluR agonist to be administered in combination with an effective amount of a disclosed compound is expected to vary from about 0.1 milligram per kilogram of body weight per day (mg/kg/day) to about 100 mg/kg/day and is expected to be less than the amount that is required to provide the same effect when administered without an effective amount of a disclosed compound. Preferred amounts of a co-administered mGluR agonist are able to be determined by one skilled in the art.

In the treatment conditions which require potentiation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed mGluR4 potentiators and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be coadministered, either in concomitant therapy or in a fixed combination.

In one aspect, the compound can be employed in combination with anti-Alzheimer's agents, beta-secretase inhibitors, gamma-secretase inhibitors, HMG-CoA reductase inhibitors, NSAIDS's (non-steroidal anti-inflammatory drugs) including ibuprofen, vitamin E, and anti-amyloid antibodies. In a further aspect, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, Zolpidem, and salts thereof, and combinations thereof, and the like, or the subject compound may be administered in conjunction with the use of physical methods such as with light therapy or electrical stimulation.

In a further aspect, the compound can be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In a further aspect, the compound can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In one aspect, the compound can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HTJA agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In the treatment of conditions which require potentiation of mGluR4 activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one aspect, the invention relates to a pharmaceutical composition comprising a compound disclosed herein or a pharmaceutically acceptable salt thereof or a pharmaceutically acceptable derivative thereof; and a pharmaceutically acceptable carrier.

In one aspect, the invention relates to pharmaceutical compositions comprising a compound having a structure represented by a compound of the following formula:

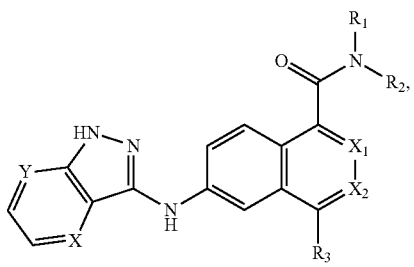

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, cyclohetroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, $CO—R_4$, $SO_2R_4$, hydroxyl, amino, aminoalkoxy, halogen, $SO_2$, $SO_2$-alkyl, $SO_2$-Me, $CONH_2$, CN, O, cycloalkyl, cyclohetroalkyl, aryl, heteroaryl;
$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cyclohetroalkyl, aryl, heteroaryl;
$R_3$ is H, alkyl, alkene, cycloalkyl, aryl, heteroaryl, alkoxy, hydroxyl, amino, aminoalkoxy, or halogen;
provided that at least one of $X_1$ or $X_2$ is N;
or a pharmaceutically acceptable salt thereof or a pharmaceutically acceptable derivative thereof; and a pharmaceutically acceptable carrier.

Also disclosed are pharmaceutical compositions comprising a compound of the following formula:

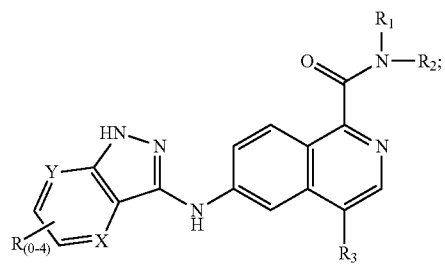

or a pharmaceutically acceptable salt thereof or a pharmaceutically acceptable derivative thereof; and a pharmaceutically acceptable carrier.

Also disclosed are pharmaceutical compositions comprising a compound of the following formula:

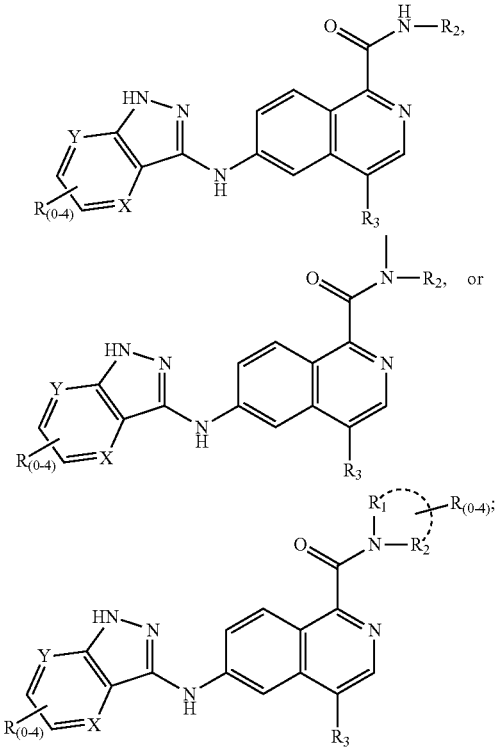

or a pharmaceutically acceptable salt thereof or a pharmaceutically acceptable derivative thereof; and a pharmaceutically acceptable carrier.

D. Methods of Using the Compounds and Compositions mGluR4 belongs to the group III mGluR subfamily and is located in predominantly in presynaptic locations in the central nervous system where it is functions as an auto- and heteroreceptor to regulate the release of both GABA and glutamate. In addition, mGluR4 is also expressed at a low level in some postsynaptic locations. mGluR4 is expressed in most brain regions, particularly in neurons known to play key roles in the following functions of the CNS:

(a) learning and memory;
(b) regulation of voluntary movement and other motor functions
(c) motor learning
(d) emotional responses
(e) habit formation, including repetitive tasks and preservative thought processes reward systems
(g) vision and olfaction
(h) cerebellar functions;
(i) feeding and the regulation of hypothalamic hormones; and
(j) sleep and wakefulness.

As such, mGluR4 plays a major role in the modulation of CNS-related diseases, syndromes and non-CNS related diseases or conditions the like, for example, (a) Parkinson's disease, parkinsonism, and other disorders involving akinesia or bradykinesia
(b) Dystonia
(c) Huntington's diseases and other disorders involving involuntary movements and dyskinesias
(d) Tourette's syndrome and related ticking disorders
(e) Obsessive/compulsive disorder and other preservative behavioral disorders Addictive disorders (including drug abuse, eating disorders, and)
(g) Schizophrenia and other psychotic disorders
(h) Posttraumatic stress disorder
(i) Anxiety disorders;
(j) motor effects after alcohol consumption or other drug-induced motor disorders;
(k) neurogenic fate commitment and neuronal survival;
(l) epilepsy;
(m) certain cancers, for example, medulloblastoma;
(n) type 2 diabetes, and/or other metabolic disorders; and
(o) taste enhancement/blockade.

The disclosed compounds can act as potentiators of the metabotropic glutamate receptor activity (mGluR4). Therefore, in one aspect, the disclosed compounds can be used to treat one or more mGluR4 associated disorders that result in dysfunction in a mammal.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone; for example, L-DOPA sparing in Parkinson's disease. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

1. Treatment Methods

The compounds disclosed herein are useful for treating, preventing, ameliorating, controlling or reducing the risk of a variety of neurological and psychiatric disorders associated with glutamate dysfunction. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more neurological and/or psychiatric disorders associated with glutamate dysfunction in a subject comprising the step of administering to the subject at least one disclosed compound; at least one disclosed pharmaceutical composition; and/or at least one disclosed product in a dosage and amount effective to treat the disorder in the subject.

Examples of disorders associated with glutamate dysfunction include: acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, multiple sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, conduct disorder, diabetes and other metabolic disorders, taste alteration, and cancer.

Anxiety disorders that can be treated or prevented by the compositions disclosed herein include generalized anxiety disorder, panic disorder, and obsessive compulsive disorder. Addictive behaviors include addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Thus, in some aspects of the disclosed method, the disorder is dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression.

Also provided is a method for treating or prevention anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

In one aspect, the invention relates to methods for the treatment of a neurotransmission dysfunction and other disease states associated with mGluR4 activity in a mammal comprising the step of administering to the mammal at least one compound of the present invention in a dosage and amount effective to treat the dysfunction in the mammal. In certain embodiments, the compound has a structure represented by the following formula:

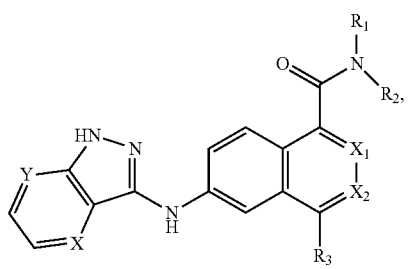

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, cycloheteroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_3$ is H, alkyl, alkene, cycloalkyl, aryl, heteroaryl, alkoxy, hydroxyl, amino, aminoalkoxy, or halogen;
provided that at least one of $X_1$ or $X_2$ is N;
or a pharmaceutically acceptable salt thereof or a pharmaceutically acceptable derivative thereof.

In one aspect, the invention relates to methods for potentiating mGluR4 activity in a subject comprising the step of administering to the subject at least one compound of the present invention in a dosage and amount effective to treat the dysfunction in the mammal. In certain embodiments, the compound has a structure represented by formula: the following formula:

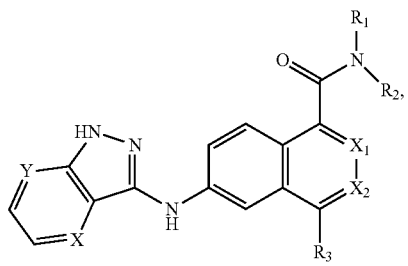

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloaklyl, cycloheteroaryl, aryl, heteroaryl, or together with $R_1$ forms a 4-7 membered ring optionally substituted with one or more R;

R is independently H, alkyl, alkene, hydroxyl, alkoxy, $CF_3$, O, O-Me, O-alkyl, O-cycloalkyl, $CO-R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_3$ is H, alkyl, alkene, cycloalkyl, aryl, heteroaryl, alkoxy, hydroxyl, amino, aminoalkoxy, or halogen;

provided that at least one of $X_1$ or $X_2$ is N;

or a pharmaceutically acceptable salt thereof or a pharmaceutically acceptable derivative thereof, in a dosage and amount effective to potentiate mGluR4 receptor activity in the subject.

In one aspect, the invention relates to methods of potentiating mGluR4 activity in at least one cell comprising the step of contacting the at least one cell with at least one compound having a structure represented by formula: the following formula:

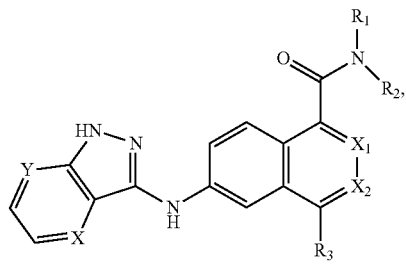

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloaklyl, cycloheteroaryl, aryl, heteroaryl, or together with $R_1$ forms a 4-7 membered ring optionally substituted with one or more R;

R is independently H, alkyl, alkene, hydroxyl, alkoxy, $CF_3$, O, O-Me, O-alkyl, O-cycloalkyl, $CO-R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_3$ is H, alkyl, alkene, cycloalkyl, aryl, heteroaryl, alkoxy, hydroxyl, amino, aminoalkoxy, or halogen;

provided that at least one of $X_1$ or $X_2$ is N;

or a pharmaceutically acceptable salt thereof or a pharmaceutically acceptable derivative thereof, in an amount effective to potentiate mGluR4 receptor activity in the at least one cell.

In certain aspects, a subject, for example a mammal or a human, has been diagnosed with the dysfunction prior to the administering step. In further aspects, a disclosed method can further comprise the step of identifying a subject, for example a mammal or a human, having a need for treatment of a dysfunction. In further aspects, a subject, for example a mammal or a human, has been diagnosed with a need for potentiation of mGluR4 receptor activity prior to the administering step. In further aspects, a disclosed method can further comprise the step of identifying a subject, for example a mammal or a human, having a need for potentiation of mGluR4 receptor activity. In further aspects, a cell (e.g., a mammalian cell or a human cell) has been isolated from a subject, for example a mammal or a human, prior to the contacting step. In further aspects, contacting is via administration to a subject, for example a mammal or a human.

In one aspect, the invention relates to methods for potentiating mGluR4 activity in at least one cell comprising the step of contacting the at least one cell with at least one disclosed compound in an amount effective to potentiate mGluR4 receptor activity in the at least one cell.

In one aspect, the invention relates to methods for potentiating mGluR4 activity in a subject comprising the step of administering to the subject a therapeutically effective amount of at least one disclosed compound in a dosage and amount effective to potentiate mGluR4 receptor activity in the subject.

In one aspect, the invention relates to methods for the treatment of a disorder associated with mGluR4 neurotransmission dysfunction or other disease state in a mammal comprising the step of administering to the mammal at least one disclosed compound in a dosage and amount effective to treat the disorder in the mammal.

The disclosed compounds can be used to treat a wide range of neurological and psychiatric disorders and other disease states associated with glutamate dysfunction. Non-limiting examples of these diseases includes movement disorders, including akinesias and akinetic-rigid syndromes (including Parkinson's disease), dystonia, epilepsy, chorea, neurogenerative diseases such as dementia, Huntington's disease, Amyotrophic Lateral Sclerosis, Alzheimer's disease, Pick's disease, Creutzfeldt-Jakob disease, pain, migraines, diabetes, obesity and eating disorders, sleep disorders including narcolepsy, and anxiety or affective disorders, including generalized anxiety disorder, panic attacks, unipolar depression, bipolar disorder, psychotic depression, and related disorders, cognitive disorders including dementia (associated with Alzheimer's disease, ischemia, trauma, stroke, HIV disease, Parkinson's disease, Huntington's disease and other general medical conditions or substance abuse), delirium, amnestic disorders, age-related cognitive decline, schizophrenia or psychosis including schizophrenia (paranoid, disorganized, catatonic or undifferentiated), schizophreniform disorder, schizoaffective disorder, delusional disorder, brief psychotic disorder, substance-related disorder, cancer and inflammation (including MS). Of the disorders above, the treatment of Parkinson's disease, movement disorders, cognitive disorders, neurodegenerative diseases, obesity and pain are of particular importance.

In one aspect, the disclosed compounds can be used to treat, or can be a component of a pharmaceutical composition used to treat movement disorders. As such, disclosed herein in a method for treating a movement disorder, comprising the step of administering to a mammal in need of treatment at least one compound in a dosage and amount effective to treat the disorder in the mammal, wherein the disorder is selected from Parkinson's disease, Huntington's disease, dystonia, Wilson's disease, chorea, ataxia, ballism, akathesia, athetosis, bradykinesia, ridigity, postural instability, inherited ataxias such as Friedreich's ataxia, Machado-Joseph disease, spinocerebellar ataxias, Tourette syndrome and other tic disorders, essential tremor, cerebral palsy, stroke, encephalopathies, and intoxication.

In a further aspect, the disclosed compounds can be used to treat, or can be a component of a pharmaceutical composition used to treat cognitive disorders. As such, disclosed herein in a method for treating a cognitive disorder, comprising the step of administering to a mammal in need of treatment at least one compound in a dosage and amount effective to treat the disorder in the mammal, wherein the disorder is selected from dementia (associated with Alzheimer's disease, ischemia, trauma, stroke, HIV disease, Parkinson's disease, Huntington's disease and other general medical conditions or substance abuse), delirium, amnestic disorders and age-related cognitive decline. The fourth edition (Revised) of the Diagnostic and Statistical Manual of Mental Disorders (DSM-IV-TR) (2000, American Psychiatric Association, Washington D.C.) provides a diagnostic tool for cognitive disorders including dementia (associated with Alzheimer's disease, ischemia, trauma, stroke, HIV disease, Parkinson's disease, Huntington's disease and other general medical conditions or substance abuse), delirium, amnestic disorders and age-related cognitive decline.

In a further aspect, the disclosed compounds can be used to treat, or can be a component of a pharmaceutical composition used to neurodegenerative disorders. As such, disclosed herein in a method for treating a neurodegenerative disorder, comprising the step of administering to a mammal in need of treatment at least one compound in a dosage and amount effective to treat a neurodegenerative disorder in the mammal.

In a still further aspect, the disclosed compounds provide a method for treating schizophrenia or psychosis. As such, disclosed herein in a method for treating a disorder related to schizophrenia or psychosis, comprising the step of administering to a mammal in need of treatment at least one compound in a dosage and amount effective to treat the disorder in the mammal, wherein the disorder related to schizophrenia or psychosis is selected from paranoid, disorganized, catatonic or undifferentiated, schizophreniform disorder, schizoaffective disorder, delusional disorder, brief psychotic disorder, substance-induced psychotic disorder. The fourth edition (Revised) of the Diagnostic and Statistical Manual of Mental Disorders (DSM-IV-TR) (2000, American Psychiatric Association, Washington D.C.) provides a diagnostic tool for c include paranoid, disorganized, catatonic or undifferentiated, schizophreniform disorder, schizoaffective disorder, delusional disorder, brief psychotic disorder, substance-induced psychotic disorder.

The subject compounds are further useful in the prevention, treatment, control, amelioration or reduction of risk of the aforementioned diseases, disorders and conditions in combination with other agents, including an mGluR agonist.

2. Coadministration Methods

The disclosed compounds may be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) may be administered by a route and in an amount commonly used therefore, contemporaneously or sequentially with a disclosed compound. When a disclosed compound is used contemporaneously with one or more other drugs, a pharmaceutical composition in unit dosage form containing such drugs and the compound is preferred. However, the combination therapy can also be administered on overlapping schedules. It is also envisioned that the combination of one or more active ingredients and a disclosed compound can be more efficacious than either as a single agent.

In one aspect, the compounds can be coadministered with anti-Alzheimer's agents, beta-secretase inhibitors, gamma-secretase inhibitors, muscarinic agonists, muscarinic potentiators HMG-CoA reductase inhibitors, NSAIDs and anti-amyloid antibodies. In a further aspect, the compounds can be administered in combination with sedatives, hypnotics, anxiolytics, antipsychotics, selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

In a further aspect, the subject compound may be used in combination with levodopa (with or without a selective extracerebral decarboxylase inhibitor), anitcholinergics such as biperiden, COMT inhibitors such as entacapone, A2a adenosine antagonists, cholinergic agonists, NMDA receptor antagonists and dopamine agonists.

In one aspect, the invention relates to methods for the treatment of a neurotransmission dysfunction and other disease states associated with mGluR4 activity in a mammal comprising the step of co-administering to the mammal at least one compound in a dosage and amount effective to treat the dysfunction in the mammal, the compound having a structure represented by the following formula:

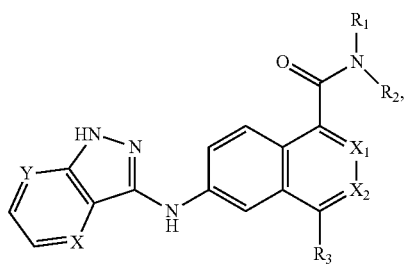

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, cycloheteroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, $CO-R_A$, $SO_2R_A$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_3$ is H, alkyl, alkene, cycloalkyl, aryl, heteroaryl, alkoxy, hydroxyl, amino, aminoalkoxy, or halogen;

provided that at least one of $X_1$ or $X_2$ is N;

or a pharmaceutically acceptable salt thereof or a pharmaceutically acceptable derivative thereof with a drug having a known side-effect of increasing metabotropic glutamate receptor activity.

In one aspect, the invention relates to methods for the treatment of a neurotransmission dysfunction and other disease states associated with mGluR4 activity in a mammal comprising the step of co-administering to the mammal at least one compound in a dosage and amount effective to treat the dysfunction in the mammal, the compound having a structure represented by the following formula:

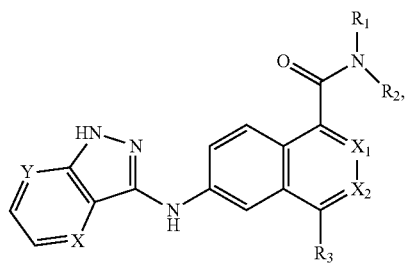

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloaklyl, cycloheteroaryl, aryl, heteroaryl, or together with $R_1$ forms a 4-7 membered ring optionally substituted with one or more R;

R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_3$ is H, alkyl, alkene, cycloalkyl, aryl, heteroaryl, alkoxy, hydroxyl, amino, aminoalkoxy, or halogen;

provided that at least one of $X_1$ or $X_2$ is N;

or a pharmaceutically acceptable salt thereof or a pharmaceutically acceptable derivative thereof with a drug known to treat a disorder associated with increasing metabotropic glutamate receptor activity.

In one aspect, the invention relates to methods for the treatment of a neurotransmission dysfunction and other disease states associated with mGluR4 activity in a mammal comprising the step of co-administering to the mammal at least one compound in a dosage and amount effective to treat the dysfunction in the mammal, the compound having a structure represented by formula: the following formula:

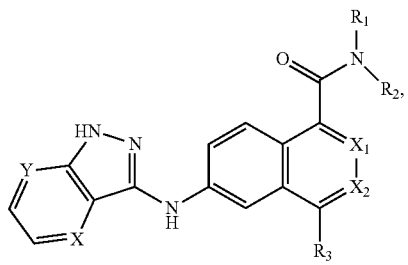

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloaklyl, cycloheteroaryl, aryl, heteroaryl, or together with $R_1$ forms a 4-7 membered ring optionally substituted with one or more R;

R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;

$R_3$ is H, alkyl, alkene, cycloalkyl, aryl, heteroaryl, alkoxy, hydroxyl, amino, aminoalkoxy, or halogen;

provided that at least one of $X_1$ or $X_2$ is N;

or a pharmaceutically acceptable salt thereof or a pharmaceutically acceptable derivative thereof with a drug known to treat the neurotransmission dysfunction and other disease states.

E. Metabotropic Glutamate Receptor Activity

The disclosed compounds and compositions can be evaluated for their ability to act as a potentiator of metabotropic glutamate receptor activity, in particular mGluR4 activity, by any suitable known methodology known in the art. For example, Chinese Hamster Ovary (CHO) cells transfected with human mGluR4 or HEK cells co-transfected with rat mGluR4 and the G-protein regulated Inwardly Rectifying Potassium channel (GIRK) were plated in clear bottom assay plates for assay in a Hamamatsu FDSS Fluorometric Plate Reader. The cells were loaded with either a Ca2+-sensitive fluorescent dye or the thallium responsive dye and the plates were washed and placed into a suitable kinetic plate reader. For human mGluR4 assays, a fluorescence baseline was established for 3-5 seconds, the disclosed compounds were then added to the cells, and the response in cells was measured. Approximately two and a half minutes later, a concentration of mGluR4 orthosteric agonist (e.g. glutamate or L-AP4) eliciting approximately 20% (EC20) of the maximal agonist response was added to the cells, and the response was measured. Two minutes later, a concentration of mGluR4 agonist (e.g. glutamate or L-AP4) eliciting 80% (EC80) of the maximal agonist response was added to the cells, and the response was measured. For rat mGluR4/ GIRK experiments, a baseline was established for approximately five seconds, disclosed compounds were added, and either an EC20 or EC80 concentration of agonist was added approximately two and one half minutes later. Potentiation of the agonist response of mGluR4 by the disclosed compounds was observed as an increase in response to the EC20 concentration of agonist in the presence of compound compared to the response to agonist in the absence of compound. Similarly, antagonism of the agonist response of mGluR4 by the disclosed compounds was observed as a decrease in response to the EC80 concentration of agonist in the presence of compound compared to the response to agonist in the absence of compound.

The above described assay operated in two modes. In the first mode, a range of concentrations of the disclosed compounds are added to cells, followed by a single fixed concentration of agonist. If the compound acts as a potentiatior, an $EC_{50}$ value for potentiation and a maximum extent of potentiation by the compound at this concentration of agonist is determined by non-linear curve fitting. If the compound acts as a noncompetitive antagonist, an $IC_{50}$ value is determined by non-linear curve fitting. In the second mode, several fixed concentrations of the disclosed compounds are added to various wells on a plate, followed by a range in concentrations of agonist for each concentration of disclosed compound. The $EC_{50}$ values for the agonist at each concentration of compound are determined by non-linear curve fitting. A decrease in the $EC_{50}$ value of the agonist with increasing concentrations of the sample compound (a leftward shift of the agonist concentration-response curve) is an indication of the degree of mGluR4 potentiation at a given concentration of the sample compound. A decrease in the maximal response of the agonist with increasing concentrations of the sample compounds, with or without a rightward shift in agonist potency, is an indication of the degree of noncompetitive antagonism at mGluR4. The second mode also indicates whether the sample compounds also affect the maximum response to mGluR4 to agonists.

In particular, the compounds of the following examples were found to have activity in potentiating the mGluR4 receptor in the aforementioned assays, generally with an $EC_{50}$ for potentiation of less than about 10 µM. One aspect of the disclosed compounds have activity in potentiating rat and human mGluR4 receptors with an $EC_{50}$ for potentiation of less than about 500 nM. These compounds further caused a leftward shift of the agonist $EC_{50}$ by greater than 3-fold. These compounds are positive allosteric modulators (potentiators) of human and rat mGluR4 and were selective for mGluR4 compared to the other seven subtypes of metabotropic glutamate receptors.

F. Manufacture of a Medicament

In one aspect, the invention relates to methods for the manufacture of a medicament for potentiating mGluR4 receptor activity in a mammal comprising combining a compound having a structure represented by formula: the following formula:

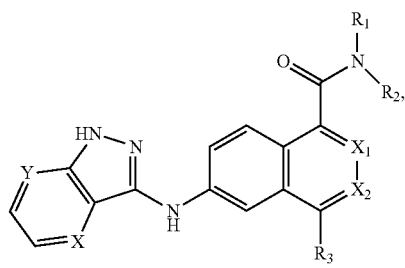

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, cycloheteroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, CO—$R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_3$ is H, alkyl, alkene, cycloalkyl, aryl, heteroaryl, alkoxy, hydroxyl, amino, aminoalkoxy, or halogen;
provided that at least one of $X_1$ or $X_2$ is N;
or a pharmaceutically acceptable salt thereof or a pharmaceutically acceptable derivative thereof with a pharmaceutically acceptable carrier.

Thus, the disclosed compounds and compositions can be further directed to a method for the manufacture of a medicament for potentiating glutamate receptor activity (e.g., treatment of one or more neurological and/or psychiatric disorder and other disease states associated with glutamate dysfunction) in mammals (e.g., humans) comprising combining one or more disclosed compounds, products, or compositions with a pharmaceutically acceptable carrier or diluent.

G. Uses of Compounds

In one aspect, the invention relates to uses of a compound for potentiating mGluR4 receptor activity in a mammal, wherein the compound has a structure represented by formula:

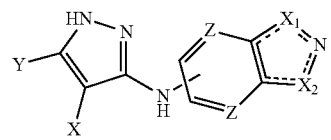

wherein X is CH, C-alkyl, N, NH, N-alkyl, alkoxy, or may form a 6-membered ring with Y optionally substituted with at least one R; Y is CH, C-alkyl, N, NH, N-alkyl, alkoxy, or may form a 6-membered ring with X optionally substituted with at least one R; Z is independently N, CH, C-alkyl, C-halogen, C-Me, C—Oalkyl, C—OMe; $X_1$ is S, C—$R_1$; C—CO—$R_1$; $X_2$ is S, C—$R_2$; C—CO—$R_2$; R is independently H, halogen, CN, Me, alkyl, alkoxy, OMe, aryl, heteroaryl, alkyl-aryl, alkyl-heteroaryl, cycloalkyl, alkyl-cycloalkyl; $R_1$ is independently H, alkoxy, amino, alkyl-alkoxy, alkyl, CN, cycloalkyl, alkyl-cycloalkyl, cycloheteroalkyl, alkyl-cycloheteroalkyl, $CF_3$, halogen, $CD_3$, $CD_2R$, $CDRR_2$, $CONR_2R_2$, aryl, heteroaryl, alkyl-aryl, alkyl-heteroaryl $SO_2R_2$, OR, $OR_2$, Oaryl, Oheteroaryl, NHR, $NR_2R_2$, fluorinated alkyl difluorinated alkyl, trifluorinated alkyl, heteroalkyl, benzyl, heteroaryl benzyl ($CH_2$heteroaryl), propanamide, diethylpropanamide, $CH_2CONR_2R_2$; $R_2$ is independently H, alkoxy, amino, alkyl-alkoxy, alkyl, CN, cycloalkyl, alkyl-cycloalkyl, cycloheteroalkyl, alkyl-cycloheteroalkyl, $CF_3$, halogen, $CD_3$, $CD_2R$, $CONR_1R_1$, aryl, heteroaryl, alkyl-aryl, alkyl-heteroaryl $SO_2R_1$, OR, $OR_1$, Oaryl, Oheteroaryl, NHR, $NR_1R_1$, fluorinated alkyl difluorinated alkyl, trifluorinated alkyl, heteroalkyl, benzyl, heteroaryl benzyl ($CH_2$heteroaryl), propanamide, diethylpropanamide, $CH_2CONR_1R_1$; or a pharmaceutically acceptable salt thereof or a pharmaceutically acceptable derivative thereof.

The disclosed uses for potentiating mGluR4 receptor activity in a mammal can further be directed for use in treating one or more disorders, for example neurological and psychiatric disorders and other disease states associated with glutamate dysfunction (e.g., Parkinson's disease) in a subject, for example a mammal or a human.

H. Kits

In one aspect, the invention relates to kits comprising a compound having a structure represented by formula: the following formula:

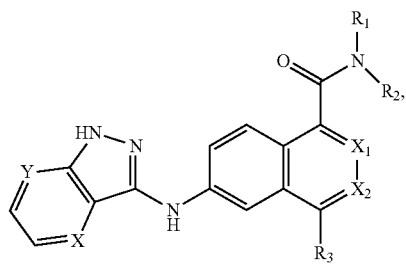

wherein the variables are substituted or unsubstituted and:
X is N, CH, CD, C-alkyl;
$X_1$ is CH, or N;
$X_2$ is CH, or N;
Y is N, CH, CD, C-alkyl;
$R_1$ is H, alkyl, aklene, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycoaklyl, cycloheteroaryl, aryl, heteroaryl, or together with $R_1$ forms a 4-7 membered ring optionally substituted with one or more R;
R is independently H, alkyl, alkene, hydroxyl, alkoxy, $CF_3$, O, O-Me, O-alkyl, O-cycloalkyl, $CO—R_4$, $SO_2R_4$, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_4$ is H, alkyl, alkene, hydroxyl, alkoxy, $CF_3$, O, O-Me, O-alkyl, O-cycloalkyl, hydroxyl, amino, aminoalkoxy, halogen, $SO_2$, $SO_2$-alkyl, $SO_2$-Me, $CONH_2$, CN, O, cycloalkyl, cycloheteroalkyl, aryl, heteroaryl;
$R_3$ is H, alkyl, alkene, cycloalkyl, aryl, heteroaryl, alkoxy, hydroxyl, amino, aminoalkoxy, or halogen;
provided that at least one of $X_1$ or $X_2$ is N;
or a pharmaceutically acceptable salt thereof or a pharmaceutically acceptable derivative thereof, and one or more of a drug having a known side-effect of increasing metabotropic glutamate receptor activity, a drug known to treat a disorder associated with increasing metabotropic glutamate receptor activity, and/or a drug known to treat the neurotransmission dysfunction and other disease states.

In various aspects, the kits can comprise disclosed compounds, compositions, and/or products co-packaged, co-formulated, and/or co-delivered with other components. For example, a drug manufacturer, a drug reseller, a physician, or a pharmacist can provide a kit comprising a disclosed oral dosage forms and another component for delivery to a patient.

In further aspects, the kits can comprise one or more other components (e.g., one or more of a drug having a known side-effect of increasing metabotropic glutamate receptor activity, a drug known to treat a disorder associated with increasing metabotropic glutamate receptor activity, and/or a drug known to treat the neurotransmission dysfunction and other disease states) and instructions for coadministration to a patient with one or more disclosed compounds, compositions, and/or products. For example, a drug manufacturer, a drug reseller, a physician, or a pharmacist can provide a kit comprising one or more other components (e.g., one or more of a drug having a known side-effect of increasing metabotropic glutamate receptor activity, a drug known to treat a disorder associated with increasing metabotropic glutamate receptor activity, and/or a drug known to treat the neurotransmission dysfunction and other disease states) and instructions for coadministration to a patient with one or more disclosed compounds, compositions, and/or products.

I. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. All NMR spectra were recorded on either a Varian Inova 400 (400 MHz) or Varian Inova 500 (500 MHz) spectrophotometer. $^1H$ chemical shifts are reported in δ values in ppm downfield from $Me_4Si$ as the internal standard in $CDCl_3$. Data are reported as follows: chemical shift, multiplicity (s=singlet, d=doublet, t=triplet, q=quartet, br=broad, m=multiplet), integration, coupling constant (Hz). $^{13}C$ chemical shifts are reported in δ values in ppm with the $CDCl_3$ carbon peak set to 77.23 ppm. Low resolution mass spectra were obtained on an HP1100 MSD with electrospray ionization. High resolution mass spectra were recorded on a Bruker Daltonics 3T Fourier transform ion cyclotron resonance mass spectrometer (FT/ICR) with electrospray ionization. Analytical thin layer chromatography was performed on EM Reagent 0.25 mm silica gel 60-F plates. Analytical HPLC was performed on an HP1100 with UV detection at 214 and 254 nm along with ELSD detection, LC/MS (J-Sphere80-C18, 3.0×50 mm, 4.1 min gradient, 5%[0.05% $TFA/CH_3CN$]:95%[0.05% $TFA/H_2O$] to 100% [0.05% $TFA/CH_3CN$]. Preparative purification was performed on a custom HP1100 purification system (reference 16) with collection triggered by mass detection. Solvents for extraction, washing and chromatography were HPLC grade. N-Boc-p-phenylenediamine was purchased from Fluka and 1,2-benzenedisulfonyl dichloride was purchased from TCI America. All other reagents were purchased from Aldrich Chemical Co. and were used without purification.

General Procedures:
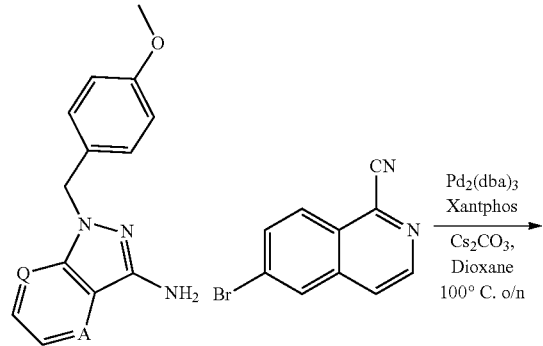
1
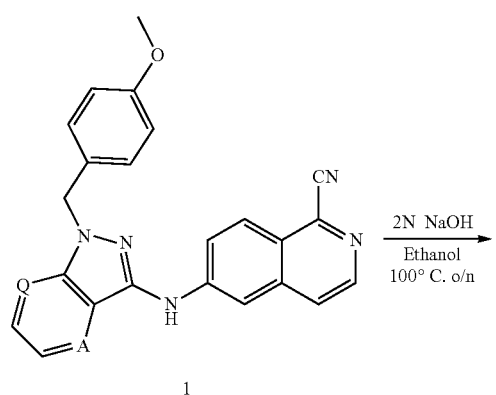
2
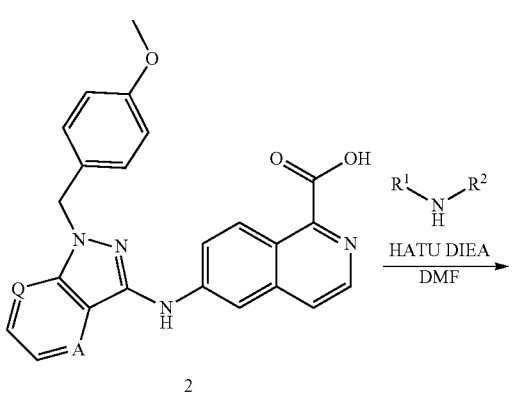
3
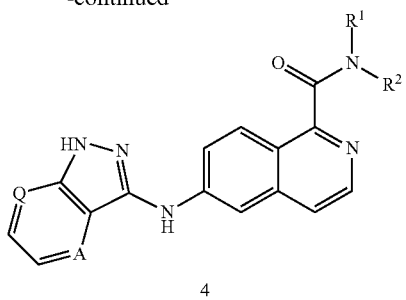
4
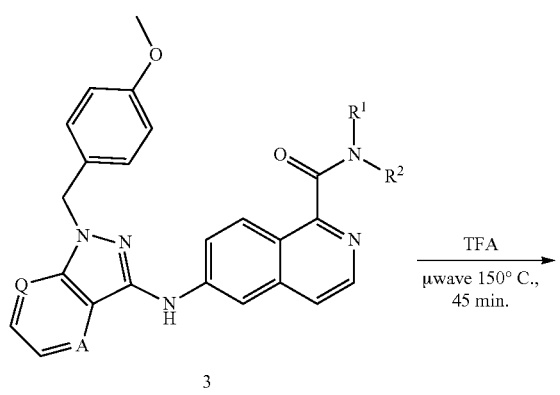
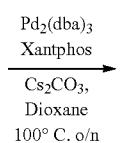

-continued

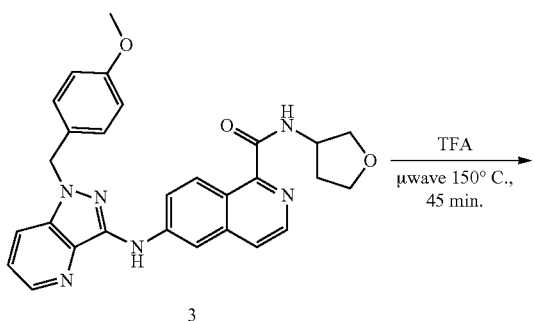

3

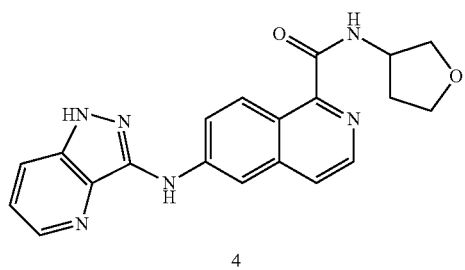

4

Schemes:

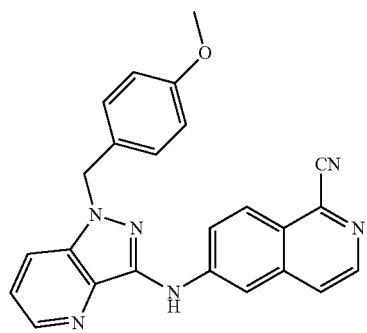 [SMILES: COc1ccc(Cn2nc(Nc3ccc4c(C#N)nccc4c3)c3ncccc32)cc1]

6-((1-(4-methoxybenzyl)-1H-pyrazolo[4,3-b]pyridin-3-yl)amino)isoquinoline-1-carbonitrile (1). 1-(4-methoxybenzyl)-1H-pyrazolo[4,3-b]pyridin-3-amine (546 mg, 2.15 mmol, 1.00 eq), 6-bromoisoquinoline-1-carbonitrile (500 mg, 2.15 mmol, 1.00 eq), 4,5-bis(diphenylphosphino)-9,9-dimethylxanthene (186 mg, 0.322 mmol, 0.150 eq), tris(dibenzylideneacetone)dipalladium(O) (196 mg, 0.215 mmol, 0.100 eq) and cesium carbonate (1.47 g, 4.51 mmol, 2.10 eq) were suspended in 1,4-dioxane (43 mL) in a sealed vial and heated at 100° C. overnight. The reaction was cooled, filtered over celite and washed with 5% methanol in DCM. The organics were concentrated and purified by flash chromatography on silica gel using 0-20% hexanes/ethyl acetate to afford 661 mg (76%) of the title compound as a yellow solid. $^1$H NMR (400 MHz, DMSO-$d_6$) δ 10.24 (s, 1H), 8.52 (s, 1H), 8.50-8.47 (m, 2H), 8.19 (d, J=8.5 Hz, 1H), 8.09 (s, 2H), 7.94 (d, J=5.7 Hz, 1H), 7.46 (dd, J=4.3, 8.5 Hz, 1H), 7.34 (d, J=8.2 Hz, 2H), 6.89 (d, J=8.3 Hz, 2H), 5.56 (s, 2H), 3.68 (s, 3H); ES-MS [M+1]$^+$: 407.2.

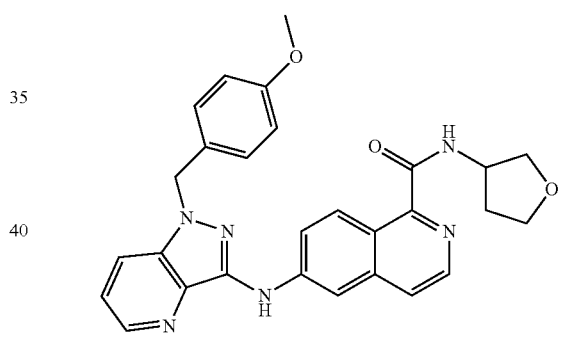

6-((1-(4-methoxybenzyl)-1H-pyrazolo[4,3-b]pyridin-3-yl)amino)isoquinoline-1-carboxylic acid (2). Compound 1 (647 mg, 1.59 mmol, 1.00 eq) was dissolved in ethanol (8 mL) and 2N NaOH (3.90 mL, 7.80 mmol, 4.90 eq) was added. The mixture was refluxed for 18 h, cooled and neutralized with 2N HCl (45 mL). The water and solvent were removed in vacuo and the crude product was used without further purification due to insolubility of the title compound. $^1$H NMR (400 MHz, DMSO-$d_6$) δ 10.43 (s, 1H), 8.88 (d, J=9.4 Hz, 1H), 8.52-8.49 (m, 2H), 8.31 (d, J=6.1 Hz, 1H), 8.21 (d, J=8.6 Hz, 1H), 8.04 (d, J=9.5 Hz, 1H), 7.97 (d, J=6.1 Hz, 1H), 7.48 (dd, J=4.2, 8.5 Hz, 1H), 7.36 (d, J=8.2 Hz, 2H), 6.89 (d, J=8.3 Hz, 2H), 5.58 (s, 2H), 3.69 (s, 3H); ES-MS [M+1]$^+$: 426.2.

6-((1-(4-methoxybenzyl)-1H-pyrazolo[4,3-b]pyridin-3-yl)amino)-N-(tetrahydrofuran-3-yl)isoquinoline-1-carboxamide (3). Compound 2 (40 mg, 0.094 mmol, 1.0 eq), 3-aminotetrahydrofuran (16 mg, 0.19 mmol, 2.0 eq), (1[bis(dimethylamino)methylene]-1H-1,2,3-triazolo[4,5-b]pyridinium 3-oxid hexafluorophosphate) (43 mg, 0.11 mmol, 1.2 eq) and N,N-diisopropylethylamine (0.033 mL, 0.19 mmol, 2.00 eq) were dissolved in DMF (1 mL) and stirred overnight. The reaction was diluted with ethyl acetate and washed with water (2×). The aqueous layer was back extracted with ethyl acetate and the combined organics were dried (MgSO$_4$), filtered and concentrated in vacuo. Purification by reverse-phase chromatography afforded 24 mg (52%) of the title compound as a yellow solid. $^1$H NMR (400 MHz, DMSO-$d_6$) δ 9.94 (s, 1H), 8.86 (d, J=6.9 Hz, 1H), 8.72 (d, J=9.4 Hz, 1H), 8.47 (d, J=3.7 Hz, 1H), 8.43 (s, 1H), 8.35 (d, J=5.5 Hz, 1H), 8.17 (d, J=8.5 Hz, 1H), 7.90 (d, J=9.3 Hz, 1H), 7.73 (d, J=5.4 Hz, 1H), 7.45 (dd, J=4.1, 8.2 Hz, 1H), 7.34 (d, J=8.1 Hz, 2H), 6.89 (d, J=8.1 Hz, 2H), 5.54 (s, 2H), 4.57-4.49 (m, 1H), 3.93-3.82 (m, 2H), 3.77-3.62 (m, 5H), 2.24-2.14 (m, 1H), 2.02-1.93 (m, 1H); ES-MS [M+1]$^+$: 495.3.

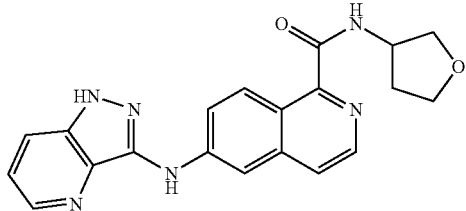 [SMILES: O=C(NC1CCOC1)c1nccc2cc(Nc3n[nH]c4cccnc34)ccc12]

6-((1H-pyrazolo[4,3-b]pyridin-3-yl)amino)-N-(tetrahydrofuran-3-yl)isoquinoline-1-carboxamide (4). Compound 3 (16 mg, 0.032 mmol, 1.00 eq) was dissolved in trifluoroacetic acid (1 mL) and heated in a microwave reactor at 150° C. for 45 minutes. The reaction was concentrated and purified by reverse-phase chromatography to afford 5 mg (41%) of the title compound as a yellow solid. $^1$H NMR (400 MHz, DMSO-$d_6$) δ 9.86 (s, 1H), 8.85 (d, J=7.0 Hz, 1H), 8.72 (d, J=9.3 Hz, 1H), 8.49-8.45 (m, 2H), 8.33 (d, J=5.7 Hz, 1H), 7.96-7.88 (m, 2H), 7.75 (d, J=5.7 Hz, 1H), 7.43 (dd, J=4.2, 8.5 Hz, 1H), 4.58-4.49 (m, 1H), 3.92-3.82 (m, 2H), 3.77-3.70 (m, 1H), 3.68-3.63 (m, 1H), 2.25-2.14 (m, 1H), 2.02-1.93 (m, 1H); ES-MS [M+1]$^+$: 375.2.

| No. | Structure | Examples used to prepare intermediate compound | ES-MS [M + 1]$^+$ |
|---|---|---|---|
| 1 | 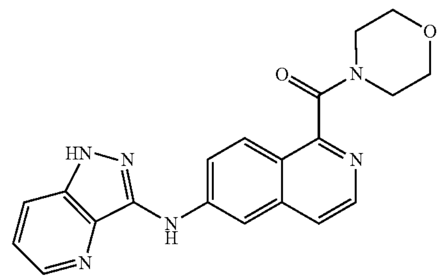 [SMILES: O=C(c1nccc2cc(Nc3n[nH]c4cccnc34)ccc12)N1CCOCC1] | 1 | 375.2 |
| 2 | 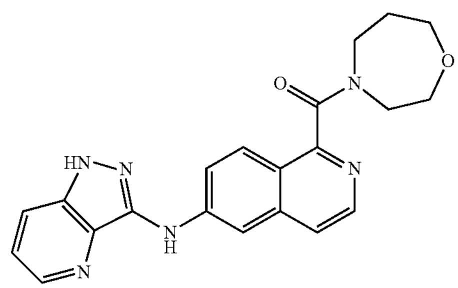 [SMILES: O=C(c1nccc2cc(Nc3n[nH]c4cccnc34)ccc12)N1CCCOCC1] | 1 | 389.2 |
| 3 | 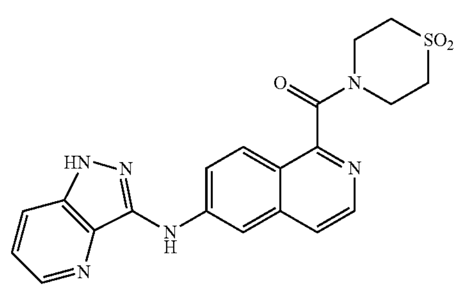 [SMILES: O=C(c1nccc2cc(Nc3n[nH]c4cccnc34)ccc12)N1CCS(=O)(=O)CC1] | 1 | 423.2 |
| 4 | 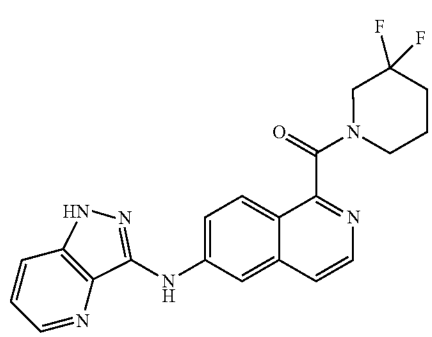 [SMILES: O=C(c1nccc2cc(Nc3n[nH]c4cccnc34)ccc12)N1CCCC(F)(F)C1] | 1 | 409.2 |

-continued

| No. | Structure | Examples used to prepare intermediate compound | ES-MS [M + 1]+ |
|---|---|---|---|
| 5 | (3-fluoropyrrolidin-1-yl)carbonyl isoquinoline with 1H-pyrazolo[4,3-b]pyridin-3-ylamino substituent | 1 | 377.2 |
| 6 | (4-(methylsulfonyl)piperazin-1-yl)carbonyl isoquinoline with 1H-pyrazolo[4,3-b]pyridin-3-ylamino substituent | 1 | 452.2 |
| 7 | (4,4-difluoropiperidin-1-yl)carbonyl isoquinoline with 1H-pyrazolo[4,3-b]pyridin-3-ylamino substituent | 1 | 409.2 |
| 8 | N-(3-fluorocyclobutyl)isoquinoline-1-carboxamide with 1H-pyrazolo[4,3-b]pyridin-3-ylamino substituent | 1 | 377.2 |
| 9 | N-(3,3-difluorocyclobutyl)isoquinoline-1-carboxamide with 1H-pyrazolo[4,3-b]pyridin-3-ylamino substituent | 1 | 395.2 |

-continued

| No. | Structure | Examples used to prepare intermediate compound | ES-MS [M + 1]+ |
| --- | --- | --- | --- |
| 10 | 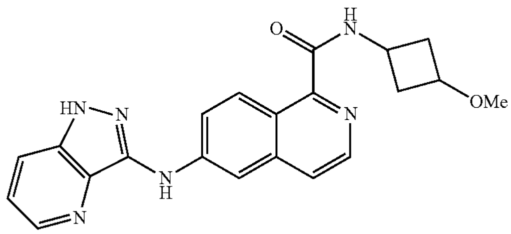 [SMILES: COC1CC(NC(=O)c2nccc3cc(Nc4n[nH]c5cccnc45)ccc23)C1] | 1 | 389.2 |
| 11 | 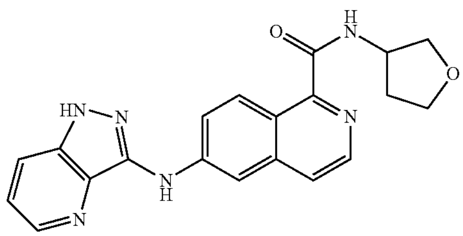 [SMILES: O=C(NC1CCOC1)c1nccc2cc(Nc3n[nH]c4cccnc34)ccc12] | 1 | 375.2 |
| 12 | 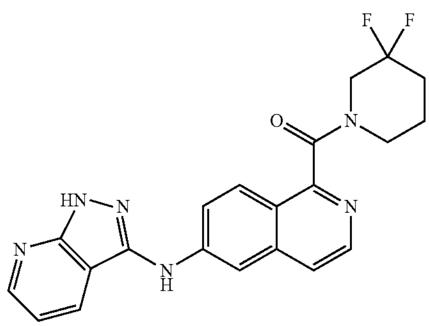 [SMILES: O=C(c1nccc2cc(Nc3n[nH]c4ncccc34)ccc12)N1CCCC(F)(F)C1] | 1 | 409.3 |
| 13 | 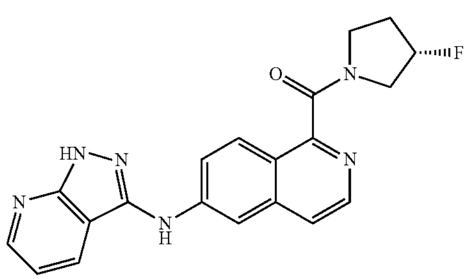 [SMILES: O=C(c1nccc2cc(Nc3n[nH]c4ncccc34)ccc12)N1CC[C@H](F)C1] | 1 | 377.3 |
| 14 | 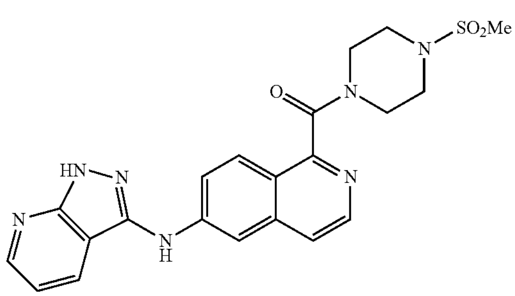 [SMILES: CS(=O)(=O)N1CCN(C(=O)c2nccc3cc(Nc4n[nH]c5ncccc45)ccc23)CC1] | 1 | 452.2 |

-continued
| No. | Structure | Examples used to prepare intermediate compound | ES-MS [M + 1]+ |
|---|---|---|---|
| 15 | 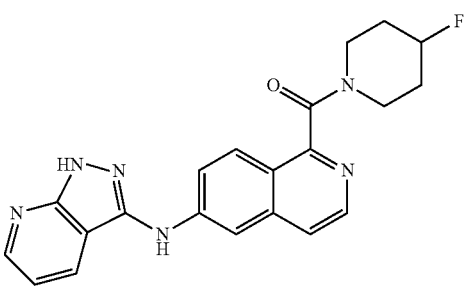 [SMILES: O=C(c1nccc2cc(Nc3n[nH]c4ncccc34)ccc12)N1CCC(F)CC1] | 1 | 391.2 |
| 16 | 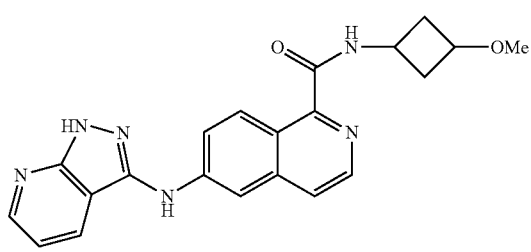 [SMILES: COC1CC(NC(=O)c2nccc3cc(Nc4n[nH]c5ncccc45)ccc23)C1] | 1 | 389.3 |
| 17 | 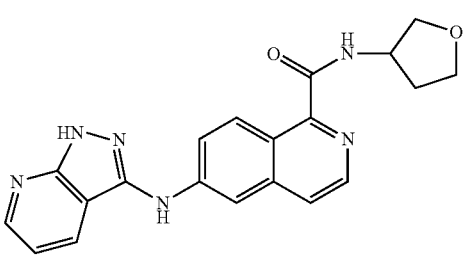 [SMILES: O=C(NC1CCOC1)c1nccc2cc(Nc3n[nH]c4ncccc34)ccc12] | 1 | 375.2 |
| 18 | 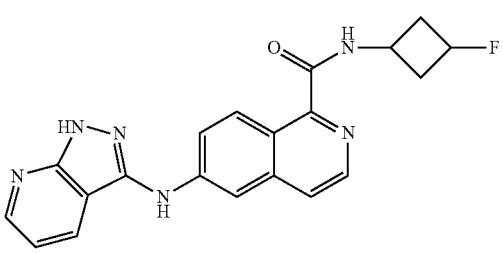 [SMILES: O=C(NC1CC(F)C1)c1nccc2cc(Nc3n[nH]c4ncccc34)ccc12] | 1 | 377.3 |
| 19 | 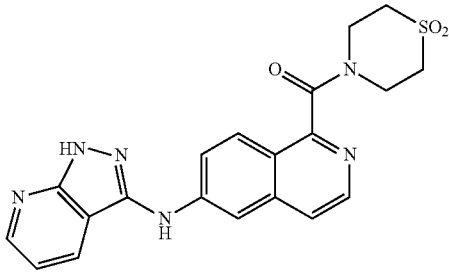 [SMILES: O=C(c1nccc2cc(Nc3n[nH]c4ncccc34)ccc12)N1CCS(=O)(=O)CC1] | 1 | 423.2 |

Further embodiments of the present invention include the following compounds:

| Compound | Structure | mGlu$_4$ PAM EC$_{50}$ (nM) | ES-MS [M + 1] |
|---|---|---|---|
| 20 | 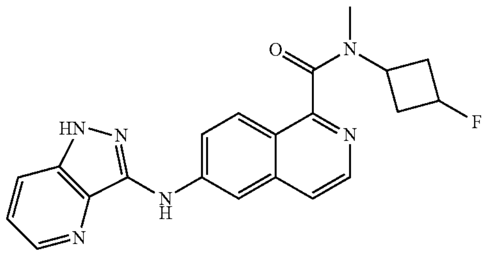 [SMILES: CN(C(=O)c1nccc2cc(Nc3n[nH]c4cccnc34)ccc12)C1CC(F)C1] | 545.9 | 391.1 |
| 22 | 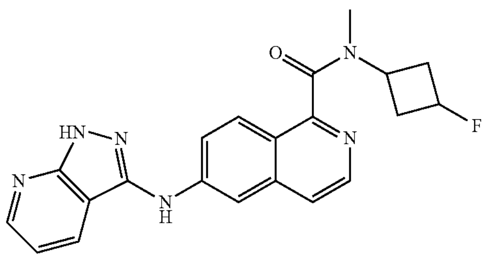 [SMILES: CN(C(=O)c1nccc2cc(Nc3n[nH]c4ncccc34)ccc12)C1CC(F)C1] | 1,799 | 391.1 |
| 23 | 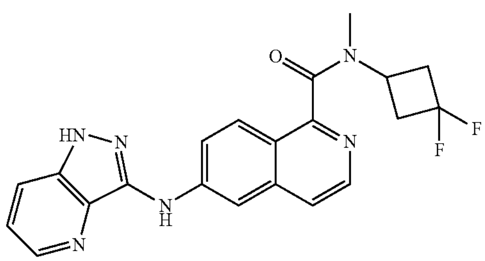 [SMILES: CN(C(=O)c1nccc2cc(Nc3n[nH]c4cccnc34)ccc12)C1CC(F)(F)C1] | 339.3 | 409.1 |
| 24 | 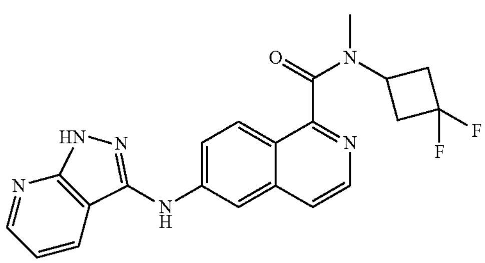 [SMILES: CN(C(=O)c1nccc2cc(Nc3n[nH]c4ncccc34)ccc12)C1CC(F)(F)C1] | 1,243 | 409.1 |
| 25 | 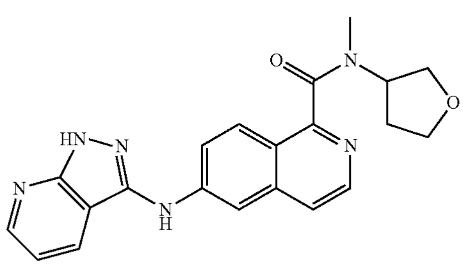 [SMILES: CN(C(=O)c1nccc2cc(Nc3n[nH]c4ncccc34)ccc12)C1CCOC1] | 4,371 | 389.1 |

-continued

| Compound | Structure | mGlu₄ PAM EC₅₀ (nM) | ES-MS [M + 1] |
|---|---|---|---|
| 26 | 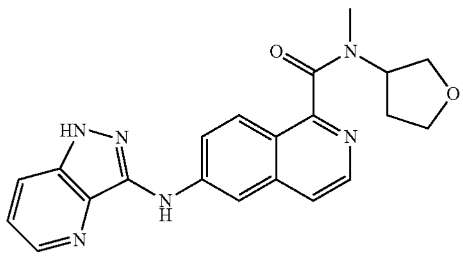 [SMILES: CN(C(=O)c1nccc2cc(Nc3n[nH]c4cccnc34)ccc12)C1CCOC1] | 1,851 | 389.1 |
| 27 | 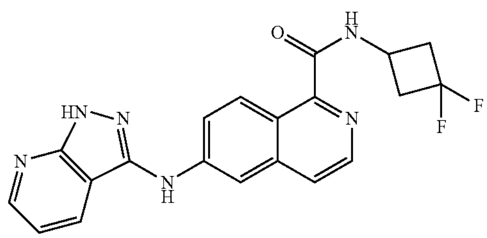 [SMILES: O=C(NC1CC(F)(F)C1)c1nccc2cc(Nc3n[nH]c4ncccc34)ccc12] | | |
| 28 | 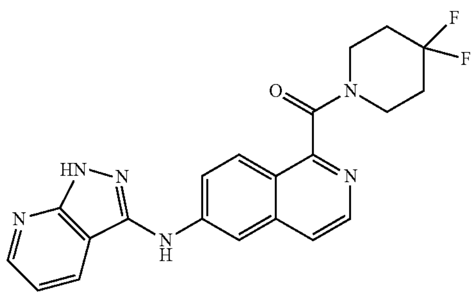 [SMILES: O=C(c1nccc2cc(Nc3n[nH]c4ncccc34)ccc12)N1CCC(F)(F)CC1] | | |

The following table shows selected in vitro drug metabolism and pharmacokinetic data. The compounds of the present invention demonstrate superior and unexpected improvements in multiple areas. For example, predicted human clearance (CLhep) is very low (CLheps=0.61 to 6.86 mL/min/kg, relative to human hepatic blood flow, CLhep=20 mL/min/kg). Additionally, the present invention demonstrates superior and unexpected uniform and robust free drug levels in rat (rfus>0.07) and human plasma (hfu>0.05) and high free drug levels in rat brain homogenate binding (rat BHB fus). As the only drug that interact with mGlu4 is free drug, the compounds of the present invention have unexpectedly exceptional profiles as putative drug candidates.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

Unless otherwise indicated, all numbers expressing quantities of ingredients, properties such as reaction conditions, and so forth used herein are to be understood as being modified in all instances by the term "about." Accordingly, unless indicated to the contrary, the numerical parameters set

| | | Human | | Rat | | Human | Rat | Rat BHB |
|---|---|---|---|---|---|---|---|---|
| hmGlu4 EC₅₀ | Example | $CL_{INT}$ | $CL_{HEP}$ | $CL_{INT}$ | $CL_{HEP}$ | $f_u$ | $f_u$ | $f_u$ |
| 1.17E−07 | 4 | 172 | 18.7 | 885 | 64.9 | 0.015 | 0.158 | 0.050 |
| 3.66E−07 | 5 | 6.91 | 5.20 | 32.5 | 22.2 | 0.094 | 0.327 | 0.095 |
| 2.68E−07 | 6 | 7.44 | 5.49 | 230 | 53.7 | 0.134 | 0.328 | 0.085 |
| 5.77E−08 | 7 | 87.4 | 16.9 | 568 | 62.3 | 0.094 | 0.168 | 0.055 |
| 2.10E−08 | 8 | 6.61 | 5.03 | 32.4 | 22.2 | 0.110 | 0.107 | 0.020 |
| 9.91E−09 | 9 | 9.01 | 6.30 | 32.8 | 22.3 | 0.090 | 0.076 | 0.010 |
| 2.55E−08 | 10 | 10.2 | 6.86 | 26.7 | 19.3 | 0.059 | 0.089 | 0.082 |
| 5.99E−08 | 11 | 0.63 | 0.61 | 2.82 | 2.71 | 0.188 | 0.229 | 0.068 |
| 5.62E−08 | 27 | 7.64 | 5.60 | 37.0 | 24.2 | 0.073 | 0.075 | 0.009 |
| 5.11E−07 | 28 | 83.4 | 16.8 | 328 | 57.7 | 0.218 | 0.179 | 0.028 | forth in the herein are approximations that may vary depending upon the desired properties sought to be determined by the present invention.

What is claimed is:

1. A compound having a structure of the following formula:

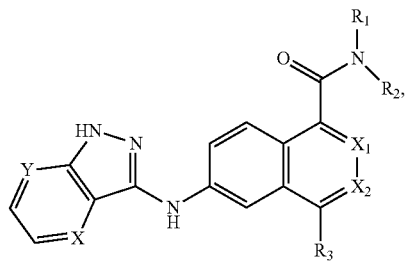

wherein the variables are substituted or unsubstituted and:
X is N,;
$X_1$ is N;
$X_2$ is CH, or N;
Y is CH, CD, C-alkyl;
$R_1$ is H, alkyl, alkenyl, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloaklyl, heterocycloalkyl, aryl, heteroaryl, or together with $R_1$ forms a 4-7 membered ring optionally substituted with one or more R;
R is independently H, alkyl, alkene, hydroxyl, alkoxy, $CF_3$, =O, O-Me, O-alkyl, O-cycloalkyl, $SO_2$-alkyl, hydroxyl, amino, aminoalkoxy, halogen, $SO_2$, $SO_2$-Me, $CONH_2$, CN, cycloalkyl, heterocycloalkyl, aryl, heteroaryl;
$R_3$ is H, alkyl, alkenyl, aryl, heteroaryl, alkoxy, hydroxyl, amino, aminoalkoxy, or halogen;
or a pharmaceutically acceptable salt thereof.

2. A compound of claim 1, of the following formula:

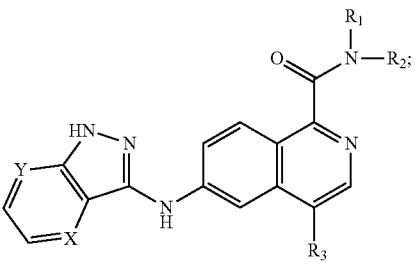

or a pharmaceutically acceptable salt thereof.

3. A compound of claim 1, of the following formula:

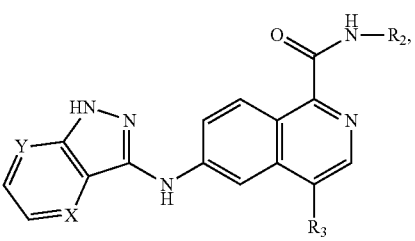

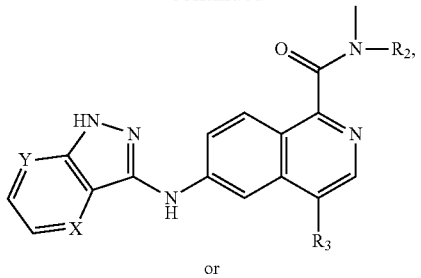

or

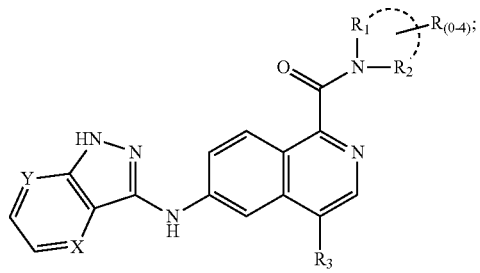

or a pharmaceutically acceptable salt thereof.

4. A compound of claim 1, wherein $R_2$ is optionally substituted with one or more R; $R_2$ being chosen from cyclobutyl, fluorocyclobutyl, difluorocyclobutyl, tetrahydrofuranyl, or tetrahydropyranyl.

5. A compound of claim 1, wherein:
cycloalkyl is cyclobutyl, cyclopropyl, cyclopentyl, cyclohexyl; and
heterocycoalkyl is piperazinyl, pyrrolidinyl, thiazepinyl, piperazinyl-ethanone, azaspiroheptanyl, oxazepanyl, tetrahydropyranyl, morpholinyl, thiomorpholinyl, dioxothiomorpholinyl.

6. A compound of claim 1, wherein:
heteroaryl is pyrazolyl, triazolyl, isoxazolyl, azetidinyl, thiophenyl, imidazolyl, and indazolyl.

7. A compound of claim 1, wherein $R_1$ and $R_2$ together form 4-7 membered cycloalkyl, or heterocycloalkyl.

8. A compound of claim 1, of the following formula:

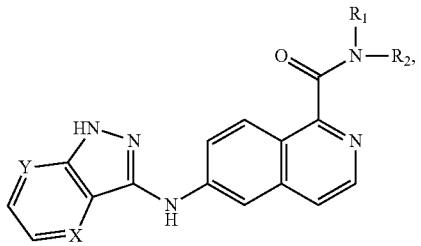

wherein:
$R_1$ is H or alkyl;
$R_2$ is

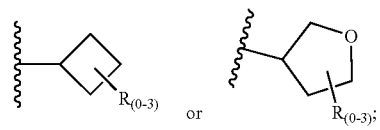

or a pharmaceutically acceptable salt thereof.

9. A compound of claim 1, of the following formula:
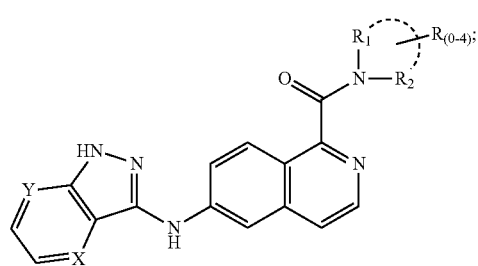
wherein:
$R_1$ and $R_2$ join together to form:
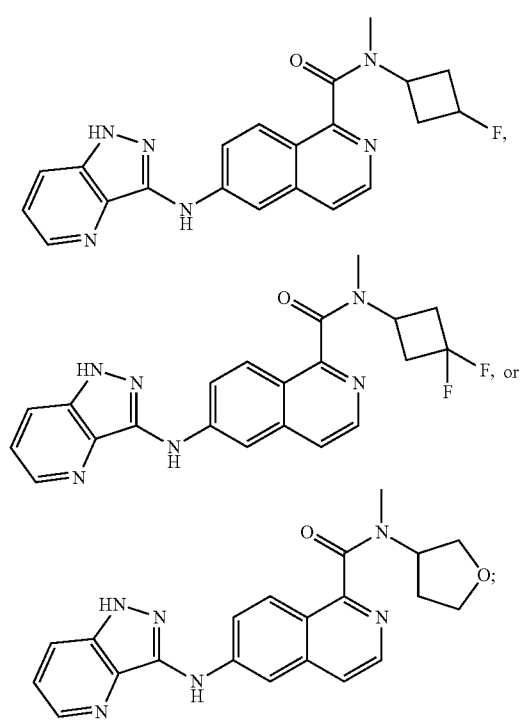
or a pharmaceutically acceptable salt thereof.
10. A compound of claim 1, of the following formula:
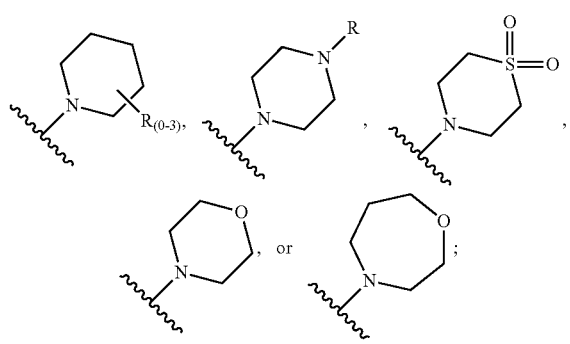
or a pharmaceutically acceptable salt thereof.
11. A compound of claim 1, of the following formula:
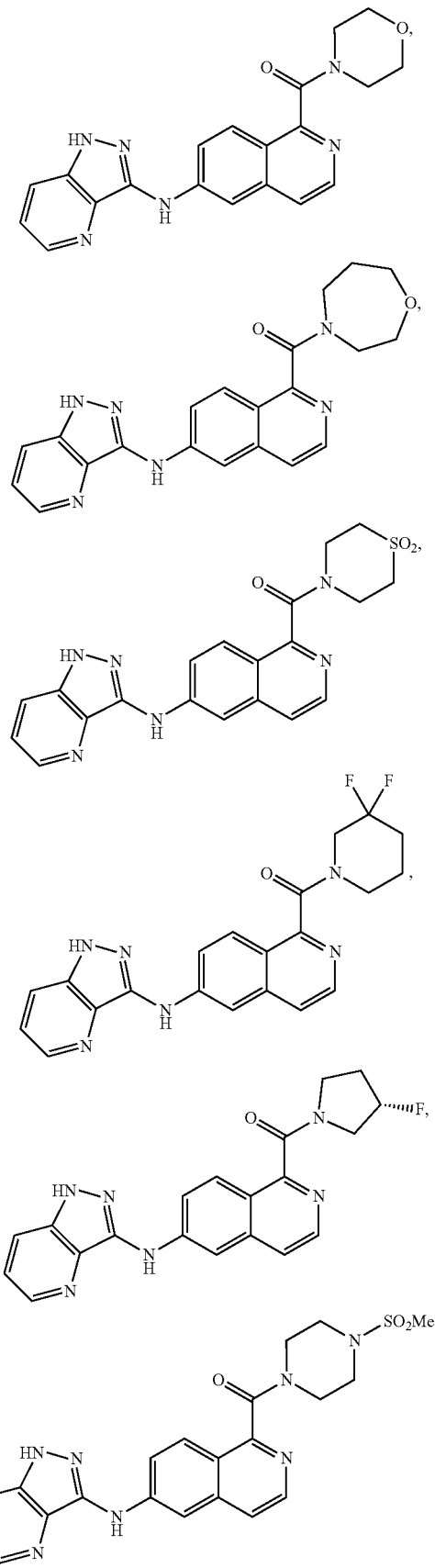

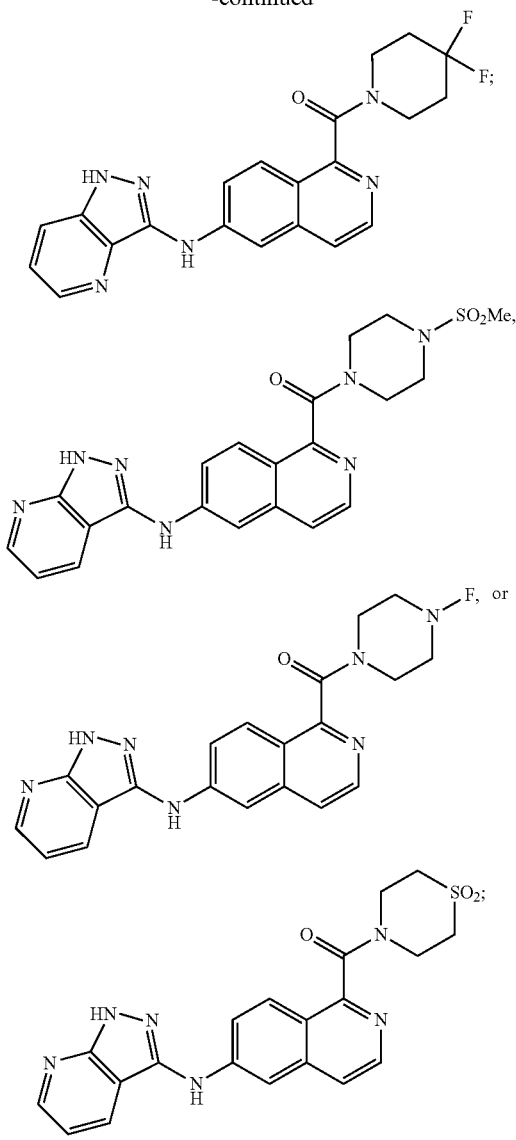

or a pharmaceutically acceptable salt thereof.

12. A compound of claim 1, of the following formula:

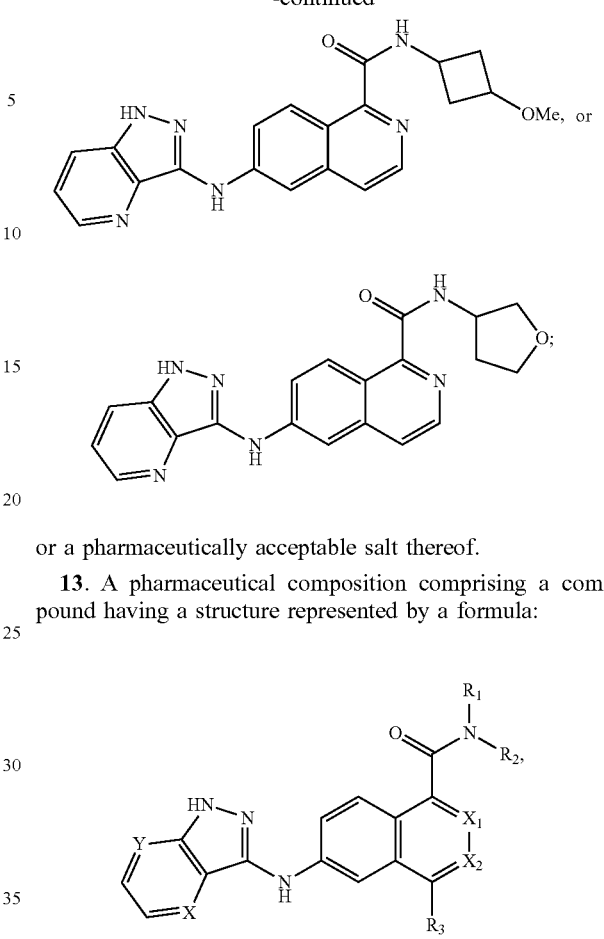

or a pharmaceutically acceptable salt thereof.

13. A pharmaceutical composition comprising a compound having a structure represented by a formula:

wherein the variables are substituted or unsubstituted and:

X is N;

$X_1$ is N;

$X_2$ is CH, or N;

Y is CH, CD, C-alkyl;

$R_1$ is H, alkyl, alkenyl, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloaklyl, heterocycloalkyl, aryl, heteroaryl, or together with $R_1$ forms a 4-7 membered ring optionally substituted with one or more R;

R is independently H, alkyl, alkenyl, hydroxyl, alkoxy, $CF_3$, =O, O-Me, O-alkyl, O-cycloalkyl, hydroxyl, amino, aminoalkoxy, halogen, $SO_2$, $SO_2$-alkyl, $SO_2$-Me, $CONH_2$, CN, cycloalkyl, heterocycloalkyl, aryl, heteroaryl;

$R_3$ is H, alkyl, alkenyl, cycloalkyl, aryl heteroaryl, alkoxy, hydroxyl, amino, aminoalkoxy, halogen;

or a pharmaceutically acceptable salt thereof and a acceptable carrier.

14. A composition of claim 13, wherein in the compound following formula:

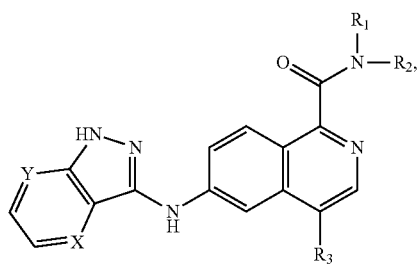

or a pharmaceutically acceptable salt thereof.

15. A composition of claim 13, wherein in the compound following formula:

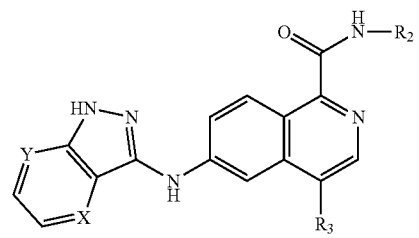

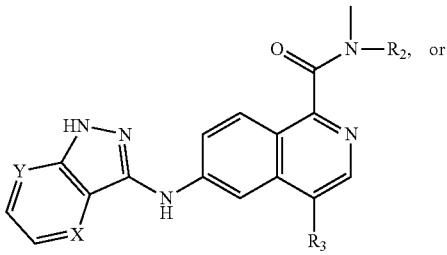

or a pharmaceutically acceptable salt thereof.

16. A composition of claim 13, wherein the compound is of the following formula:

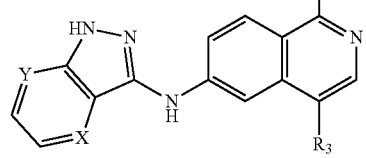
(I)

wherein:
(I) $R_1$ is H or alkyl; $R_2$ is

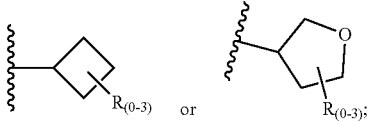

or

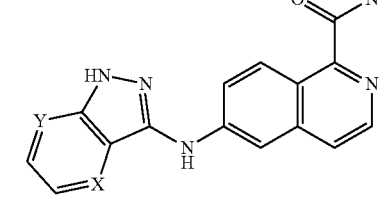
(II)

wherein:
$R_1$ and $R_2$ join together to form:

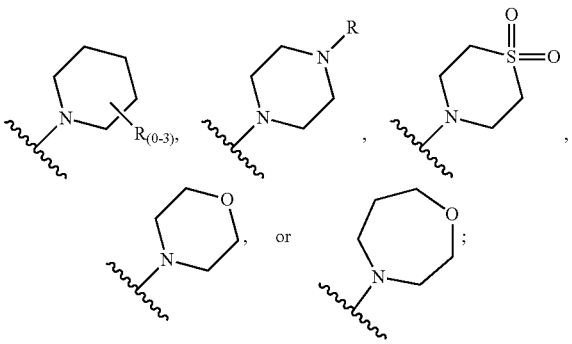

or a pharmaceutically acceptable salt thereof.

17. A compound of claim 1, of the following formula:

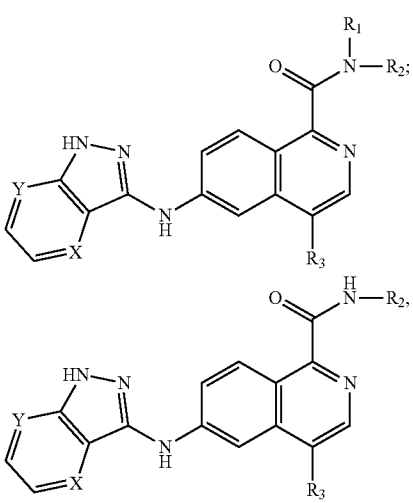

-continued

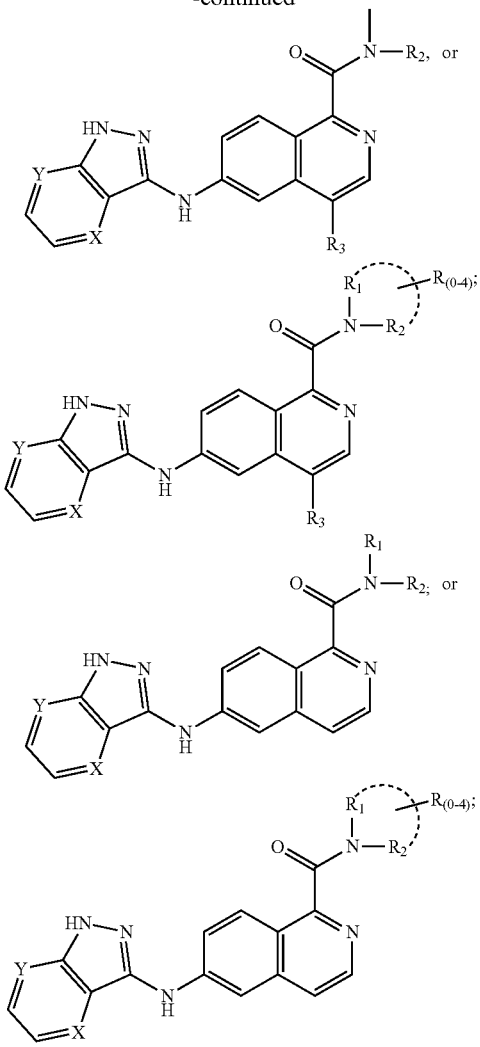

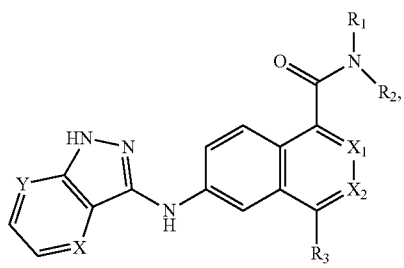

or a pharmaceutically acceptable salt thereof.

18. A compound having a structure of the following formula:

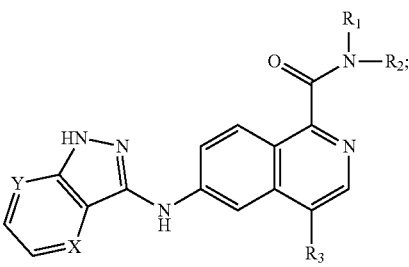

wherein the variables are substituted or unsubstituted and:
X is CH, CD, C-alkyl;
$X_1$ is N;
$X_2$ is CH, or N;
Y is N;
$R_1$ is H, alkyl, alkenyl, cycloalkyl, halogen, $CF_3$, alkoxy, OH, CN, Oalkyl, $CH_2F$, $CHF_2$, or together with $R_2$ forms a 4-7 membered ring optionally substituted with one or more R;

$R_2$ is optionally substituted with one or more R, and is chosen from cycloalkyl, heterocycloalkyl, aryl, heteroaryl, or together with $R_1$ forms a 4-7 membered ring optionally substituted with one or more R;

R is independently H, alkyl, alkenyl, hydroxyl, alkoxy, $CF_3$, $O_2$, O-Me, O-alkyl, O-cycloalkyl, $SO_2$-alkyl, hydroxyl, amino, aminoalkoxy, halogen, $SO_2$, $SO_2$-Me, $CONH_2$, CN, cycloalkyl, heterocycloalkyl, aryl, heteroaryl;

$R_3$ is H, alkyl, alkenyl, cycloalkyl, aryl, heteroaryl, alkoxy, hydroxyl, amino, aminoalkoxy, or halogen;

or a pharmaceutically acceptable salt thereof.

19. A compound of claim 18, of the following formula:

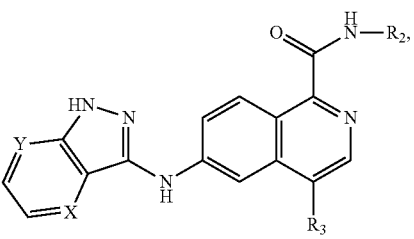

or a pharmaceutically acceptable salt thereof.

20. A compound of claim 18, of the following formula:

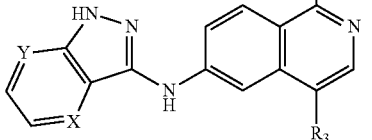

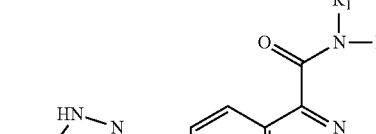

or a pharmaceutically acceptable salt thereof.

21. A compound of claim 18, wherein $R_2$ is optionally substituted with one or more R; $R_2$ being chosen from cyclobutyl, fluorocyclobutyl, difluorocyclobutyl, tetrahydrofuranyl, or tetrahydropyranyl.

22. A compound of claim 18, wherein:
cycloalkyl is cyclobutyl, cyclopropyl, cyclopentyl, cyclohexyl; and
heterocycloalkyl is piperazinyl, pyrrolidinyl, thiazepinyl, piperazinyl-ethanone, azaspiroheptanyl, oxazepanyl, tetrahydropyranyl, morpholinyl, thiomorpholinyl, dioxothiomorpholinyl.

23. A compound of claim 18, wherein:
heteroaryl is pyrazolyl, triazolyl, isoxazolyl, azetidinyl, thiophenyl, imidazolyl, and indazolyl.

24. A compound of claim 1, wherein $R_1$ and $R_2$ together form 4-membered cycloalkyl.

25. A compound of claim 18, of the following formula:

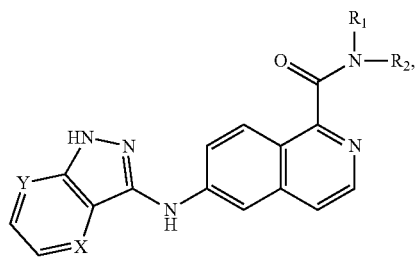

wherein:
$R_1$ is H or alkyl;
$R_2$ is

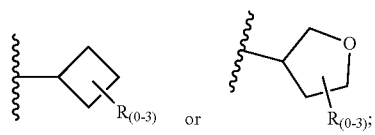

or a pharmaceutically acceptable salt thereof.

26. A compound of claim 18, of the following formula:

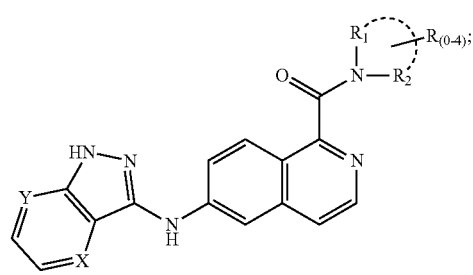

wherein:
$R_1$ and $R_2$ join together to form:

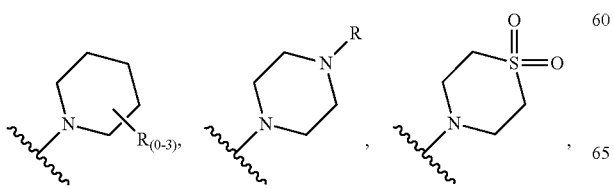

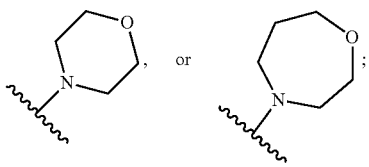

or a pharmaceutically acceptable salt thereof.

27. A compound of claim 18, of the following formula:

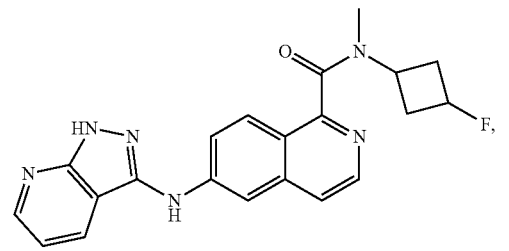

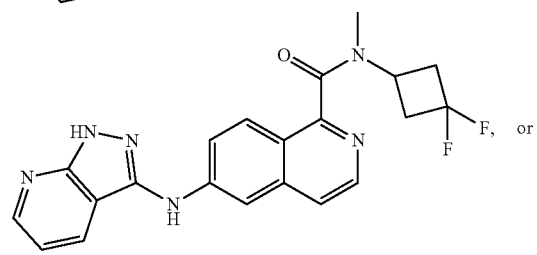

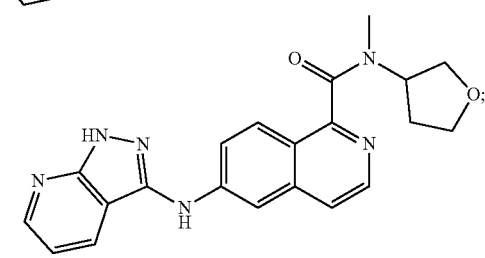

or a pharmaceutically acceptable salt thereof.

28. A compound of claim 18, of the following formula:

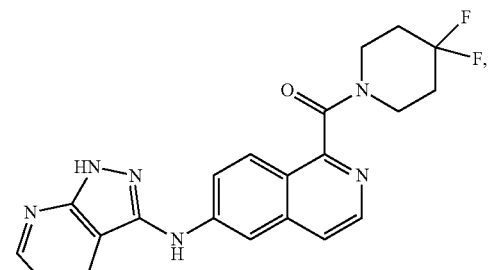

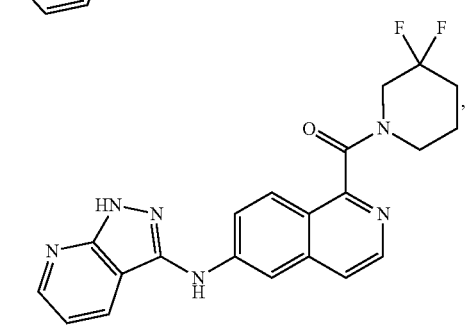

81

-continued

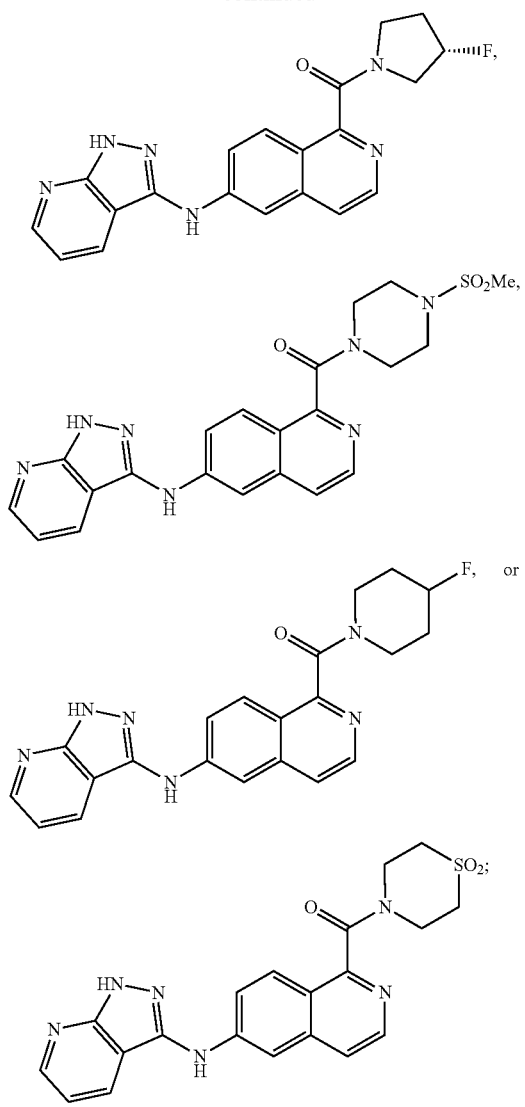

or a pharmaceutically acceptable salt thereof.

29. A compound of claim 18, of the following formula:

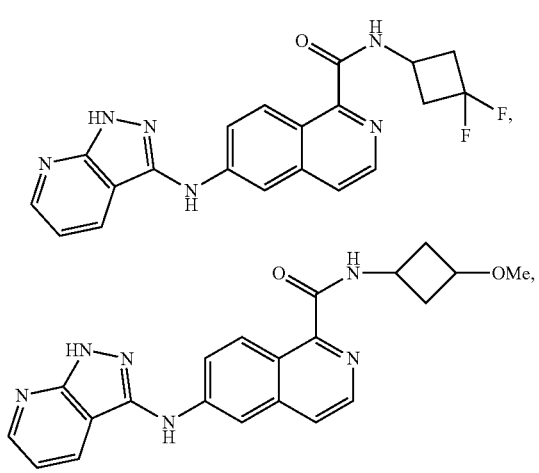

82

-continued

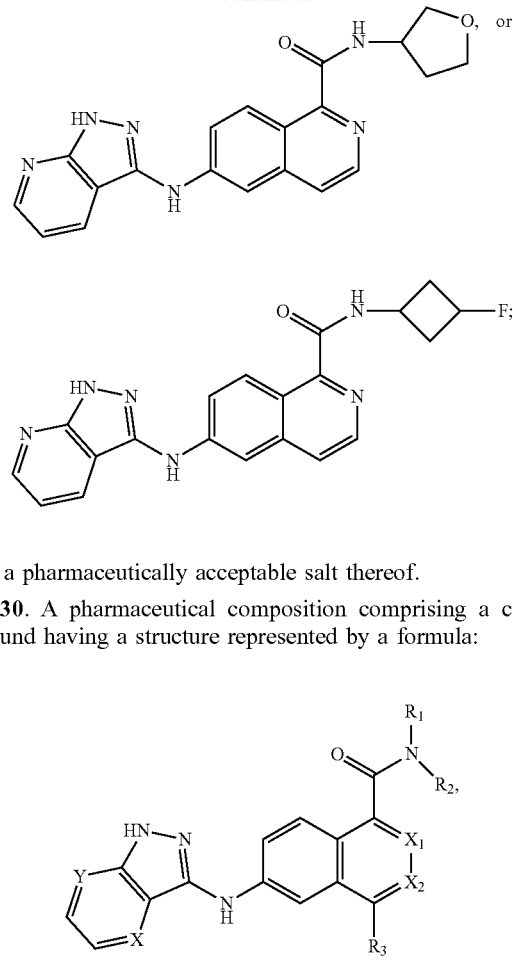

or a pharmaceutically acceptable salt thereof.

30. A pharmaceutical composition comprising a compound having a structure represented by a formula:

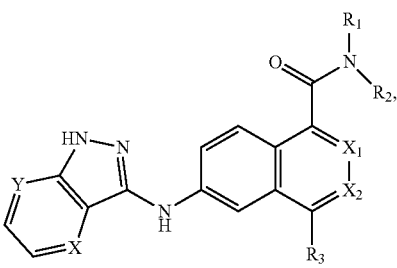

wherein the variables are substituted or unsubstituted and:
X is CH, CD, C-alkyl;
$X_1$ is N;
$X_2$ is CH, or N;
Y is N;
$R_1$ is H, alkyl, alkenyl, cycloalkyl, halogen, $CF_3$, alkoxy, OH, CN, Oalkyl, $CH_2F$, $CHF_2$, or together with $R_2$ forms a 4-7 membered ring optionally substituted with one or more R;
$R_2$ is optionally substituted with one or more R, and is chosen from cycloalkyl, heterocycloalkyl, aryl, heteroaryl, or together with $R_1$ forms a 4-7 membered ring optionally substituted with one or more R;
R is independently H, alkyl, alkenyl, hydroxyl, alkoxy, $CF_3$, $O_2$, O-Me, O-alkyl, O-cycloalkyl, hydroxyl, amino, aminoalkoxy, halogen, $SO_2$, $SO_2$-alkyl, $SO_2$-Me, $CONH_2$, CN, cycloalkyl, heterocycloalkyl, aryl, heteroaryl;
$R_3$ is H, alkyl, alkenyl, cycloalkyl, aryl, heteroaryl, alkoxy, hydroxyl, amino, aminoalkoxy, or halogen;
or a pharmaceutically acceptable salt thereof, and a pharmaceutically acceptable carrier.

31. A composition of claim 30, wherein in the compound following formula:

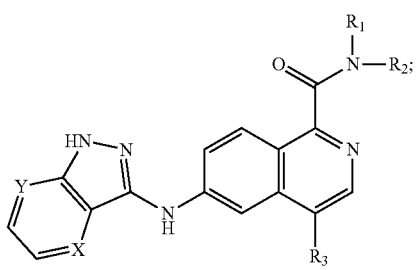

or a pharmaceutically acceptable salt thereof.

32. A composition of claim 30, wherein in the compound following formula:

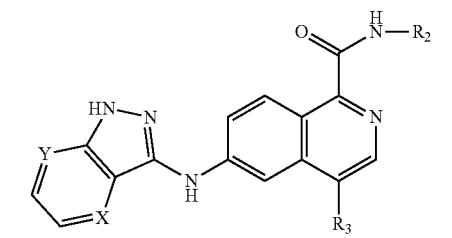

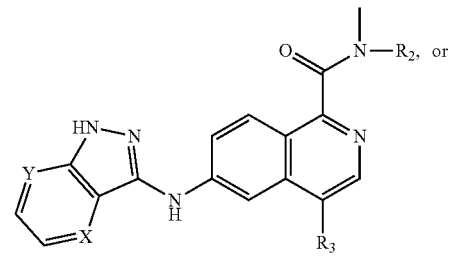

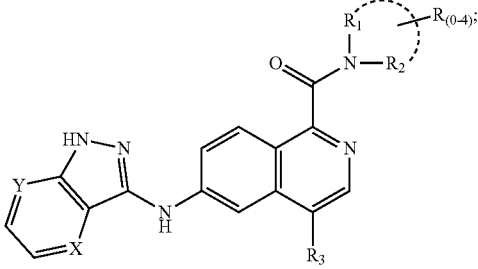

or a pharmaceutically acceptable salt thereof.

33. A composition of claim 30, wherein the compound is of the following formula:

(I)

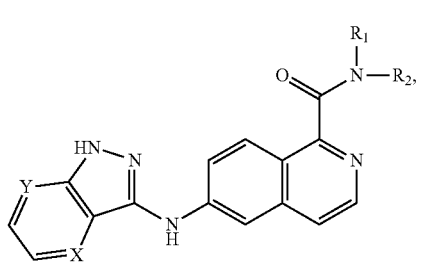

wherein:
(I) $R_1$ is H or alkyl; $R_2$ is

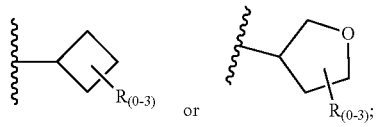

or (II)

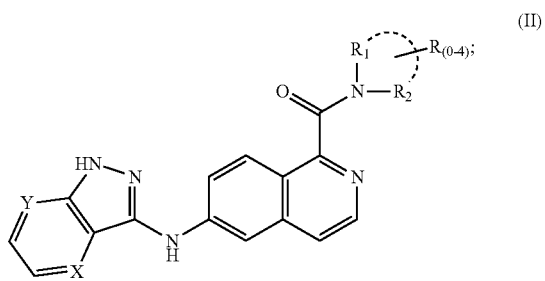

wherein:
$R_1$ and $R_2$ join together to form:

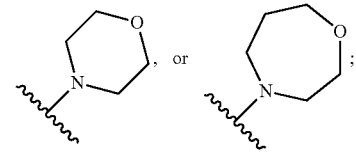

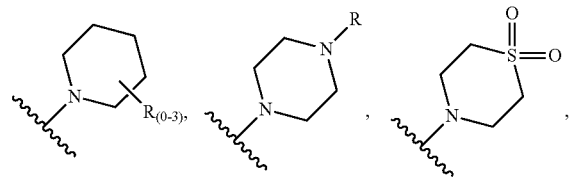

or a pharmaceutically acceptable salt thereof.

34. A compound of claim 18, of the following formula:

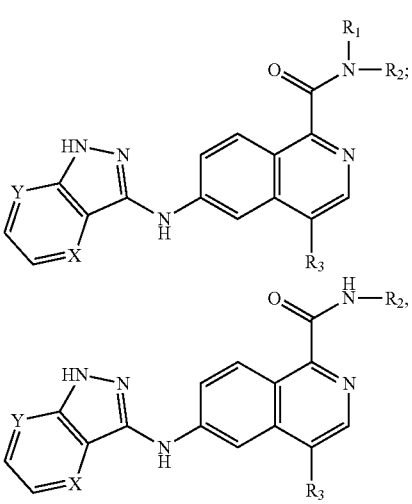

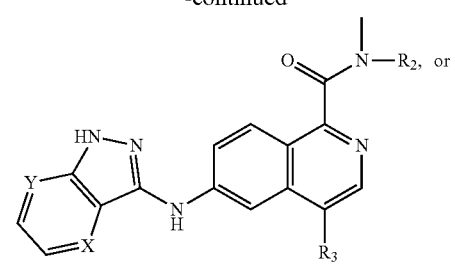
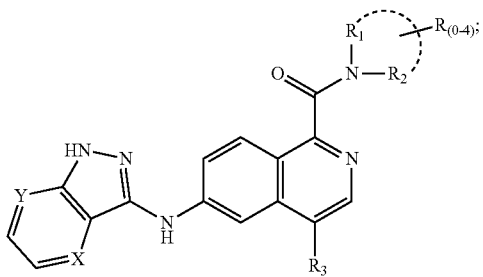
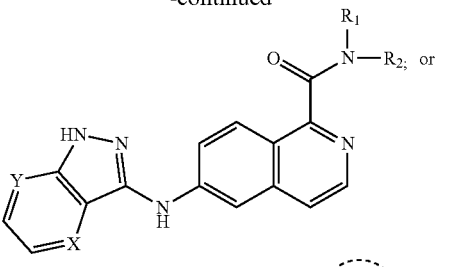
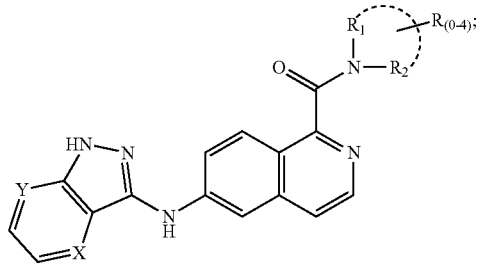
or a pharmaceutically acceptable salt thereof.
* * * * *